United States Patent [19]

Mookherjee et al.

[11] 4,145,354
[45] Mar. 20, 1979

[54] PROCESS FOR PREPARING 5-ACYL-2-(FURFURYLTHIO)DIHYDRO-2,5-DIALKYL-3-[2H]FURANONES

[75] Inventors: Braja D. Mookherjee, Holmdel; Donald A. Withycombe, Lincroft; Ira Katz, West Long Branch, all of N.J.; Alfred E. Goossens, New York, N.Y.; Manfred H. Vock, Locust, N.J.; William J. Evers, Middletown, N.J.; Joaquin F. Vinals, Red Bank, N.J.; Jacob Kiwala, Brooklyn, N.Y.

[73] Assignee: International Flavors & Fragrances Inc., New York, N.Y.

[21] Appl. No.: 887,637

[22] Filed: Mar. 17, 1978

Related U.S. Application Data

[62] Division of Ser. No. 819,957, Jul. 28, 1977, Pat. No. 4,092,334.

[51] Int. Cl.² .................................... C07D 307/64
[52] U.S. Cl. .................................... 260/347.2
[58] Field of Search ............................ 260/347.2

[56] References Cited

U.S. PATENT DOCUMENTS 3,985,907  10/1976  Evers et al. ................... 426/535

Primary Examiner—Richard Raymond
Attorney, Agent, or Firm—Arthur L. Liberman; Franklin D. Wolffe

[57] ABSTRACT

Processes and compositions are described for the use in foodstuff, chewing gum, toothpaste and medicinal product flavor and aroma and tobacco flavor and aroma augmenting, modifying, enhancing and imparting compositions and as foodstuff, chewing gum, toothpaste, medicinal product and tobacco aroma and flavor imparting, augmenting, modifying and enhancing materials of one or more 5-acyl-2-(furfurylthio)dihydro-2,5-dialkyl-3-[2H]furanones having the generic structure:

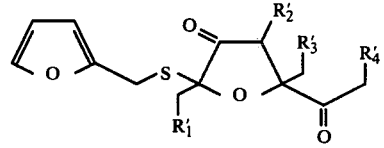

wherein $R_1'$, $R_2'$, $R_3'$ and $R_4'$ are each the same or different and each represents hydrogen or methyl produced according to the process of reacting one or more alpha, beta diketones containing from 4 up to 6 carbon atoms and having the generic structure:

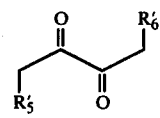

or one or more dimerization products thereof having the generic structure:

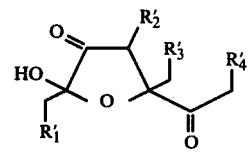

wherein $R_1'$, $R_2'$, $R_3'$, $R_4'$, $R_5'$ and $R_6'$ are each the same or different and each represents hydrogen or methyl with furfuryl mercaptan having the structure:

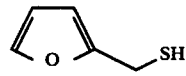

Addition of one or more 5-acyl-2-(furfurylthio)dihydro-2,5-dialkyl-3-[2H]furanones or "cis" or "trans" isomers thereof to consumable materials is indicated to produce:
(A) In flavoring compositions for foodstuffs, chewing gums, toothpastes and medicinal products and in the foodstuffs, chewing gums, toothpastes, and medicinal products per se, coffee, roasted, cocoa-like, caramel-like, licorice and roasted almond aroma and flavor characteristics at levels of greater than or equal to 0.01 parts per million; and (B) In tobacco, flavoring compositions for tobacco, tobacco substitutes and flavoring compositions therefor, wheat, caramel/coffee aroma and taste characteristics prior to and on smoking and nutty/pyrazine-like flavor and aroma characteristics with roasted nut like nuances on smoking.

1 Claim, 9 Drawing Figures

GC PROFILE FOR EXAMPLE I

FIG.6 MASS SPECTRUM FOR EXAMPLE I, PEAK I, ISOMER "A"

MASS SPECTRUM FOR EXAMPLE I, PEAK 2, ISOMER "B"

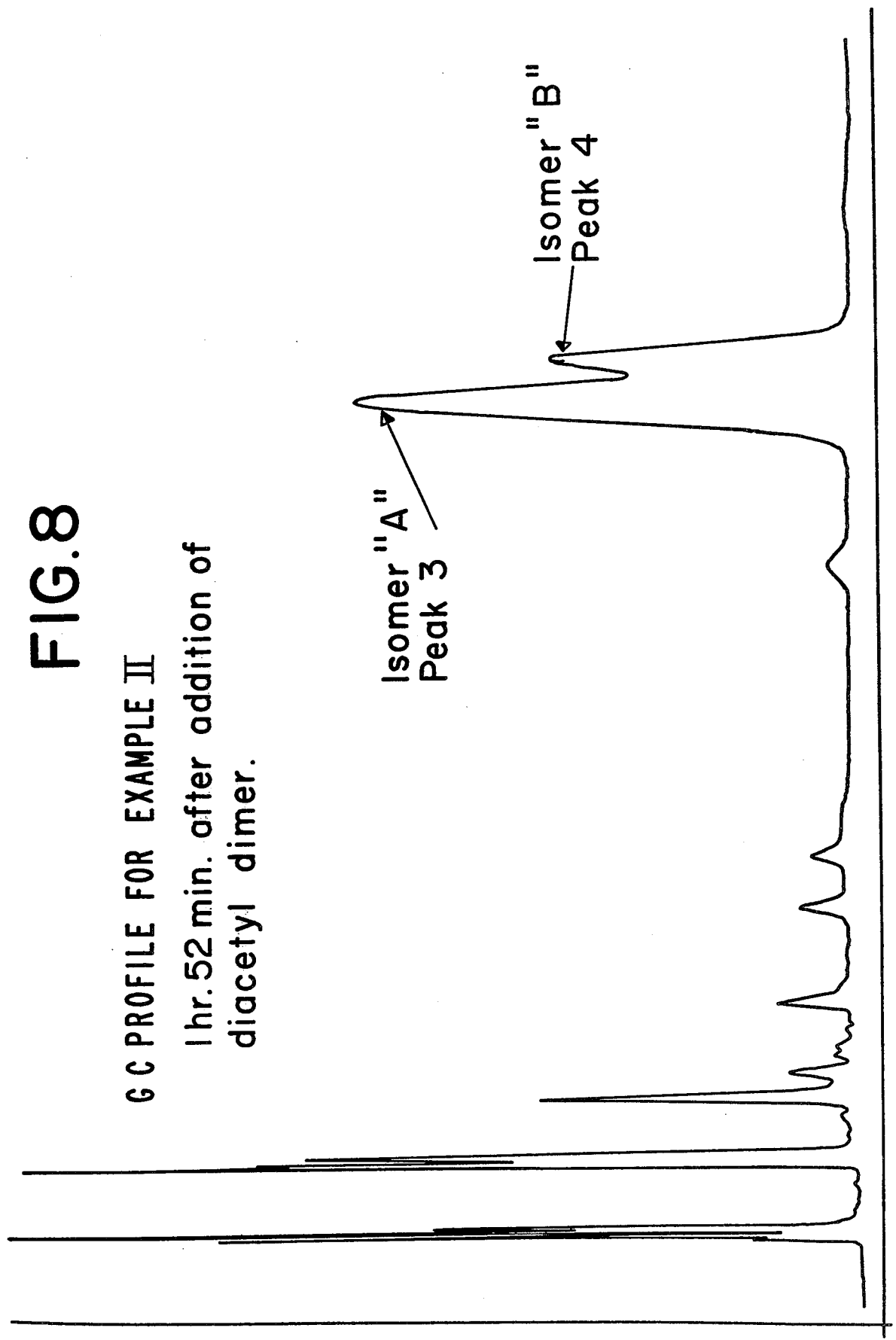

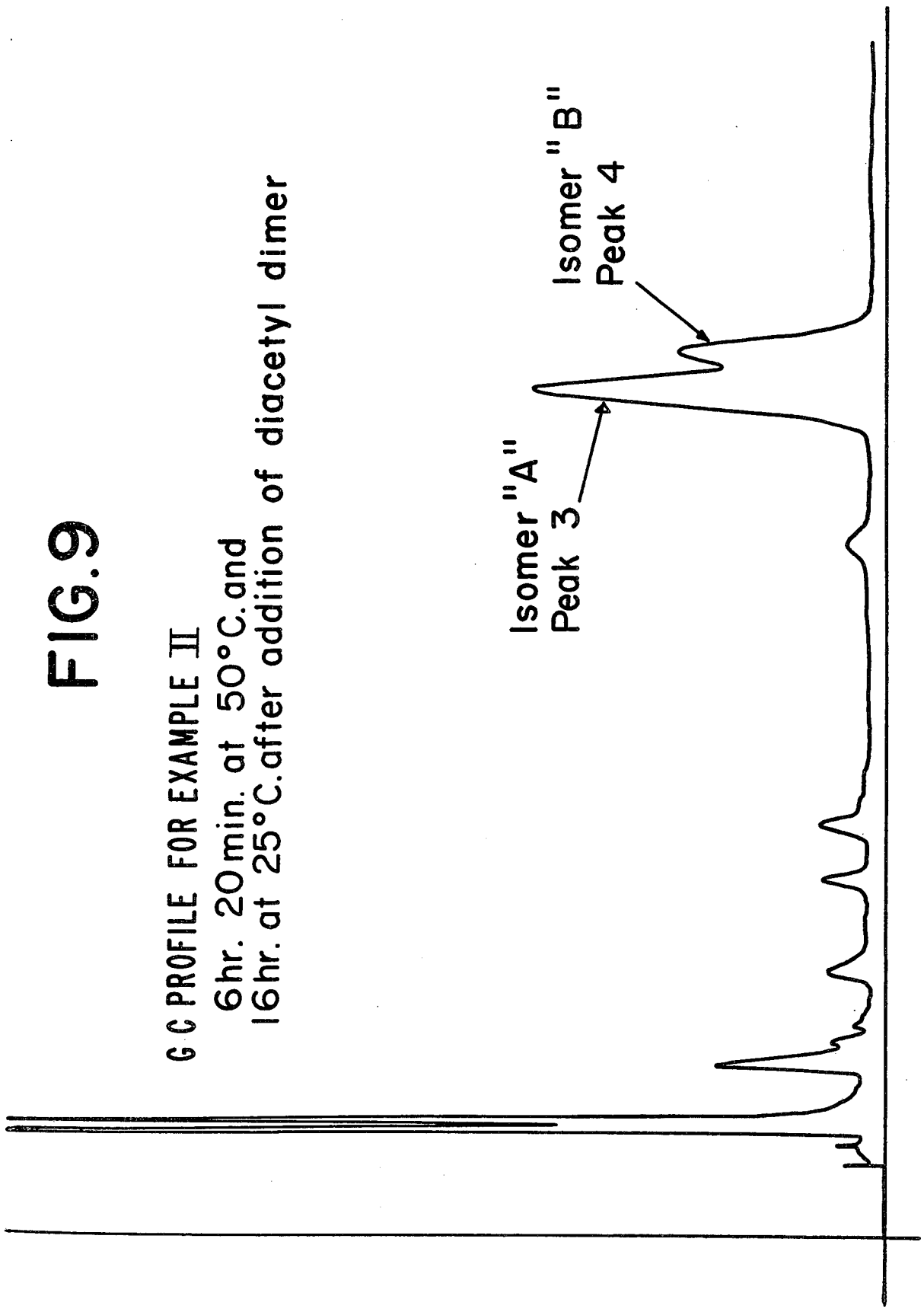

PROCESS FOR PREPARING 5-ACYL-2-(FURFURYLTHIO)DIHYDRO-2,5-DIALKYL-3-[2H]FURANONES

This application is a divisional of application for United States Letters Patent, Serial No. 819,957, filed on July 28, 1977, now U.S. Pat. No. 4,092,334, issued on May 30, 1978.

BACKGROUND OF THE INVENTION

The present invention relates to 5-acyl-2-(furfurylthio) dihydro-2,5-dialkyl-3-[2H]furanones produced by the process more particularly disclosed and claimed in copending application for U.S. Letters Patent, Ser. No. 819,889 filed on July 28, 1977 (Title: "Process For Preparing 5-acyl-2-(furfurylthio)dihydro-2,5-dialkyl-3-[2H]furanones") and novel compositions using one or more of such 5-acyl-2-(furfurylthio)dihydro-2,5-dialkyl-3-[2H]furanones or "cis" or "trans" isomers thereof to alter, modify, augment or enhance the flavor and/or aroma of consumable materials or impart flavor and/or aroma to consumable materials.

There has been considerable work performed relating to substances which can be used to impart (modify, augment or enhance) flavors to (or in) various consumable materials. These substances are used to diminish the use of natural products, some of which may be in short supply and to provide more uniform properties in the finished product. Coffee-like, roasted, cocoa-like, caramel-like, licorice, and roasted almond aroma and flavor characteristics are particularly desirable for many uses in foodstuff flavors, chewing gum flavors, toothpaste flavors and medicinal product flavors. Sweet, caramel/coffee aromas and flavors prior to smoking and sweet, caramel/coffee, nutty/pyrazine and roasted nutty aroma and taste characteristics on smoking are particularly desirable in tobaccos as well as tobacco flavoring compositions and in tobacco substitutes and flavoring compositions for such tobacco substitutes.

When one mole of diactyl is reacted with one mole of furfuryl mercaptan a coffee flavored reaction product is produced which has been discovered by us to contain a small percentage (about 10% by weight) of 5-acyl-2-(furfurylthio)dihydro-2,5-dimethyl-3-[2H]furanone with one of the "cis" - "trans" isomers being in a ratio to the other of the "cis" - "trans" isomers in about 2:1. The process for preparing such a reaction product (without describing the constituents of the products) is set forth in Swiss Patent #128,720 published on Nov. 16, 1928. It is stated in the example at column 2 on page 1 thereof that when one mixes furfuryl-2-mercaptan and diacetyl the product (alpha-oxy-alpha-acetylethyl)furfuryl-2-sulfide is produced. There is no disclosure in Swiss Patent #128,720 that an additional mole of diacetyl added to the resulting reaction product will produce the compound having the structure:

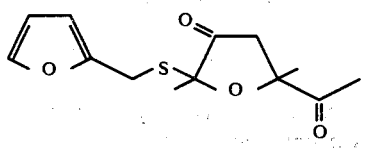

and
or any of its "cis" or "trans" isomers having the structures:

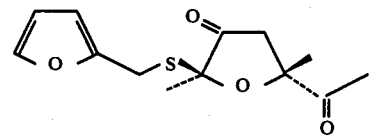

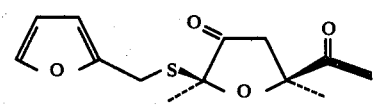

In addition there is no disclosure either explicit or implicit in Swiss Patent #128,720 that the compound having
the structure:

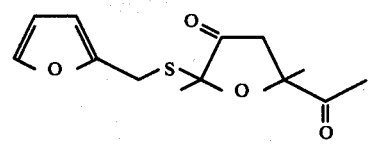

can be produced having a very high intensity and long lasting aroma and taste characteristics of the nature described herein.

U.S. Pat. No. 1,696,419 issued on Dec. 25, 1928 (Title: "Method of Producing Artificial coffee Aroma") discloses the production of a coffee flavor using: "one part of diacetyl, four parts of acetyl propionyl, four parts of methyl ethyl acetaldehyde, three parts of acetaldehyde, two parts of alpha methyl furfural, one part of furfural, three parts of pyridine, two parts of isovaleric acid, one part of phenol, one part of isoeugenol, 0.5 parts of guiacol, 0.5 parts of alpha methyl cyclopentenolone, 0.6 parts of methyl mercaptan, 0.3 parts of furfuryl mercaptan, 0.3 parts of n-octyl alcohol and 0.4 parts of thioguiacol" at page 3, column 1, lines 29–39.

The compound having the structure:

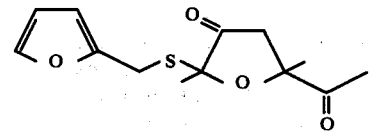

is not indicated to be produced as a result of admixing at higher temperatures the foregoing ingredients.

Nothing in the prior art discloses the reaction of one or more dimers of alpha, beta diketones having from 4 up to 6 carbon atoms with furfuryl mercaptan to form the genus of compounds having the structure:

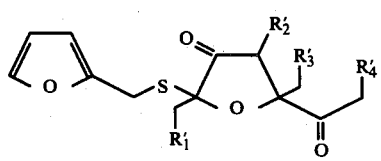

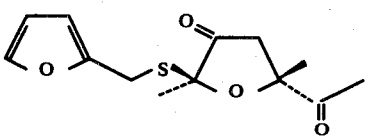

or

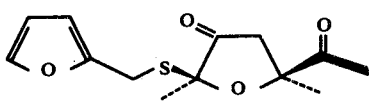

Figure 2:
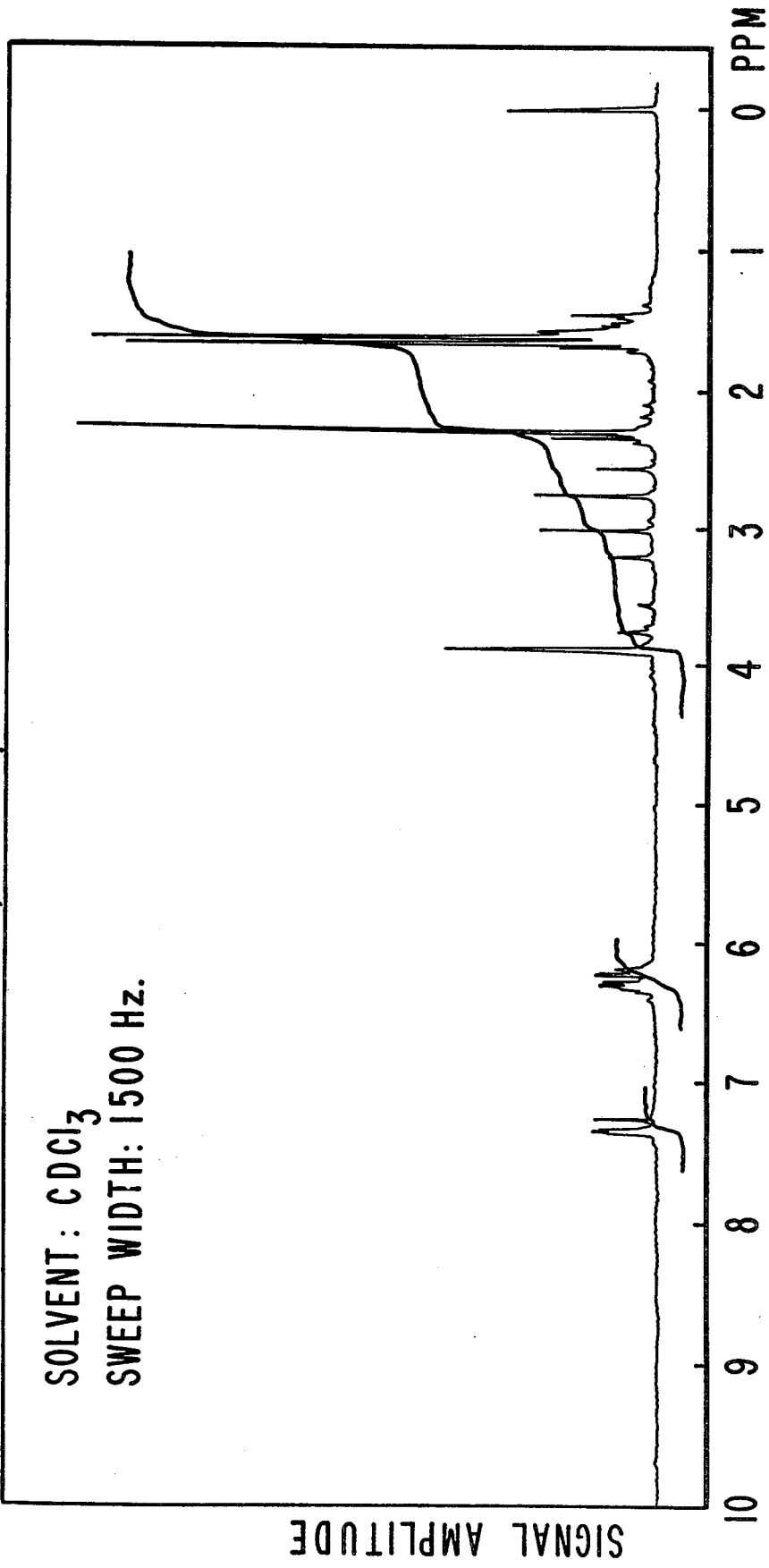

FIG. 2 represents the NMR spectrum for isomer "B", peak 2, produced according to the processs of Example I and is the spectrum for the compounds having one of the structures:

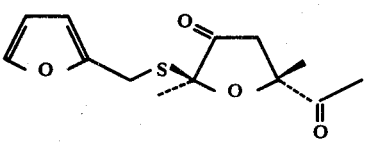

or

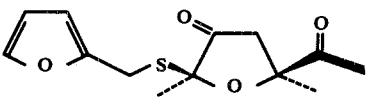

Figure 3:
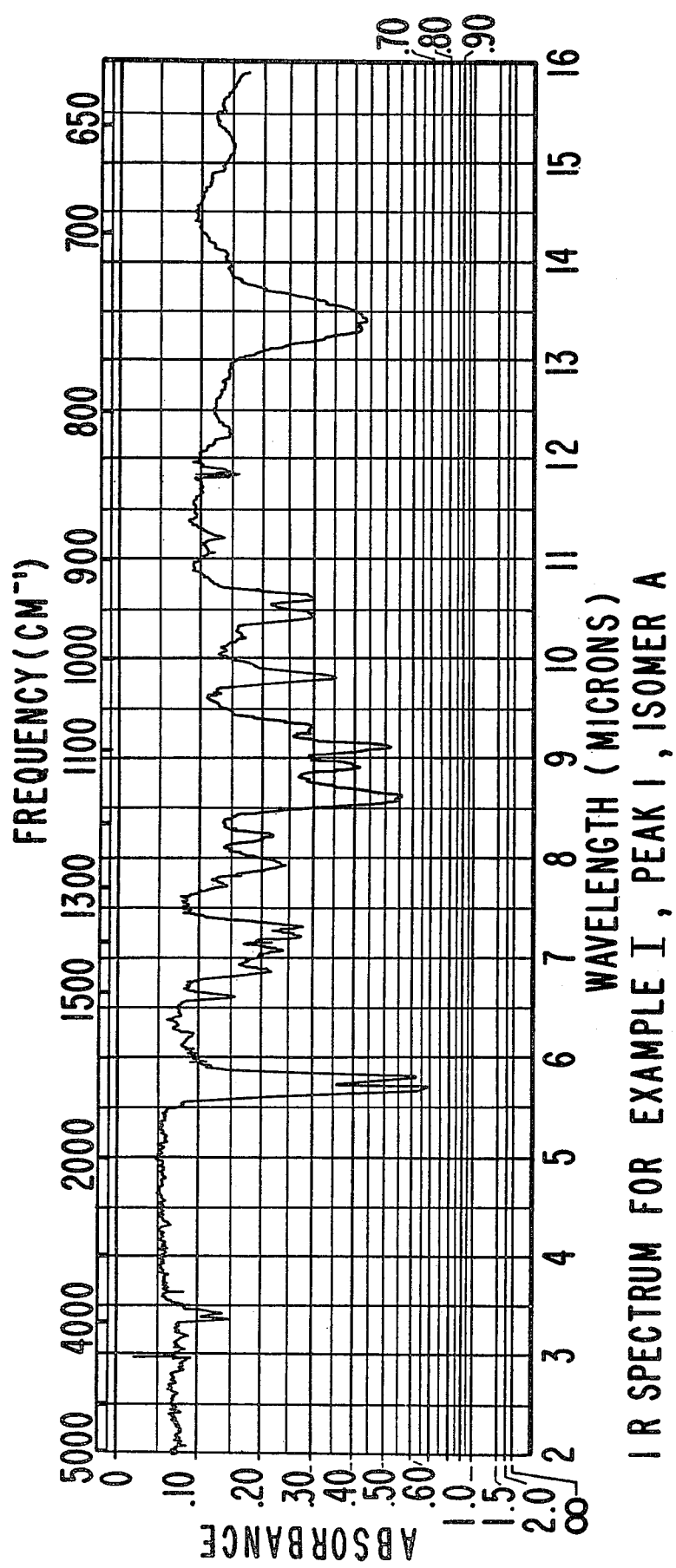

FIG. 3 is the infrared spectrum for isomer "A", peak 1, of the reaction product produced according to Example I.

Figure 4:
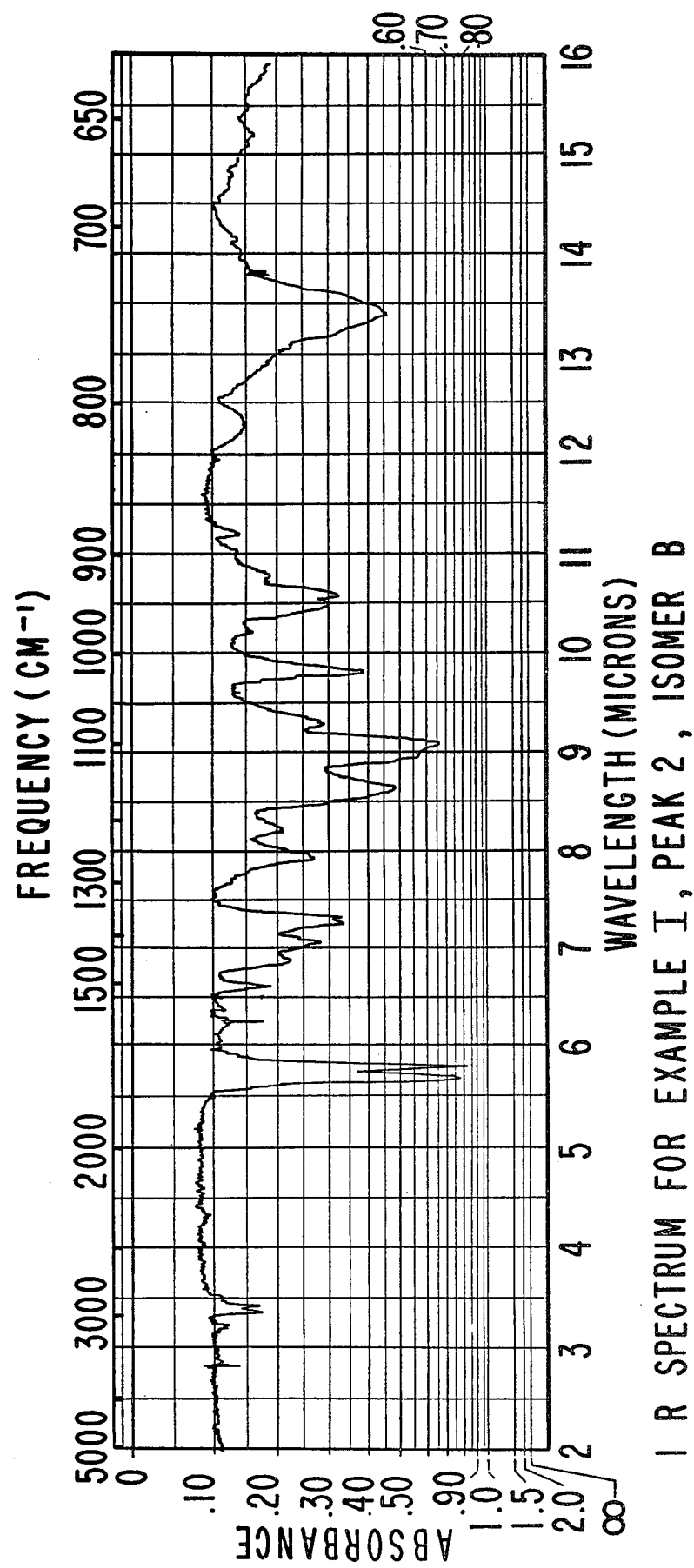

FIG. 4 represents the infrared spectrum for isomer "B", peak 2, of the reaction product produced according to Example I.

Figure 5:
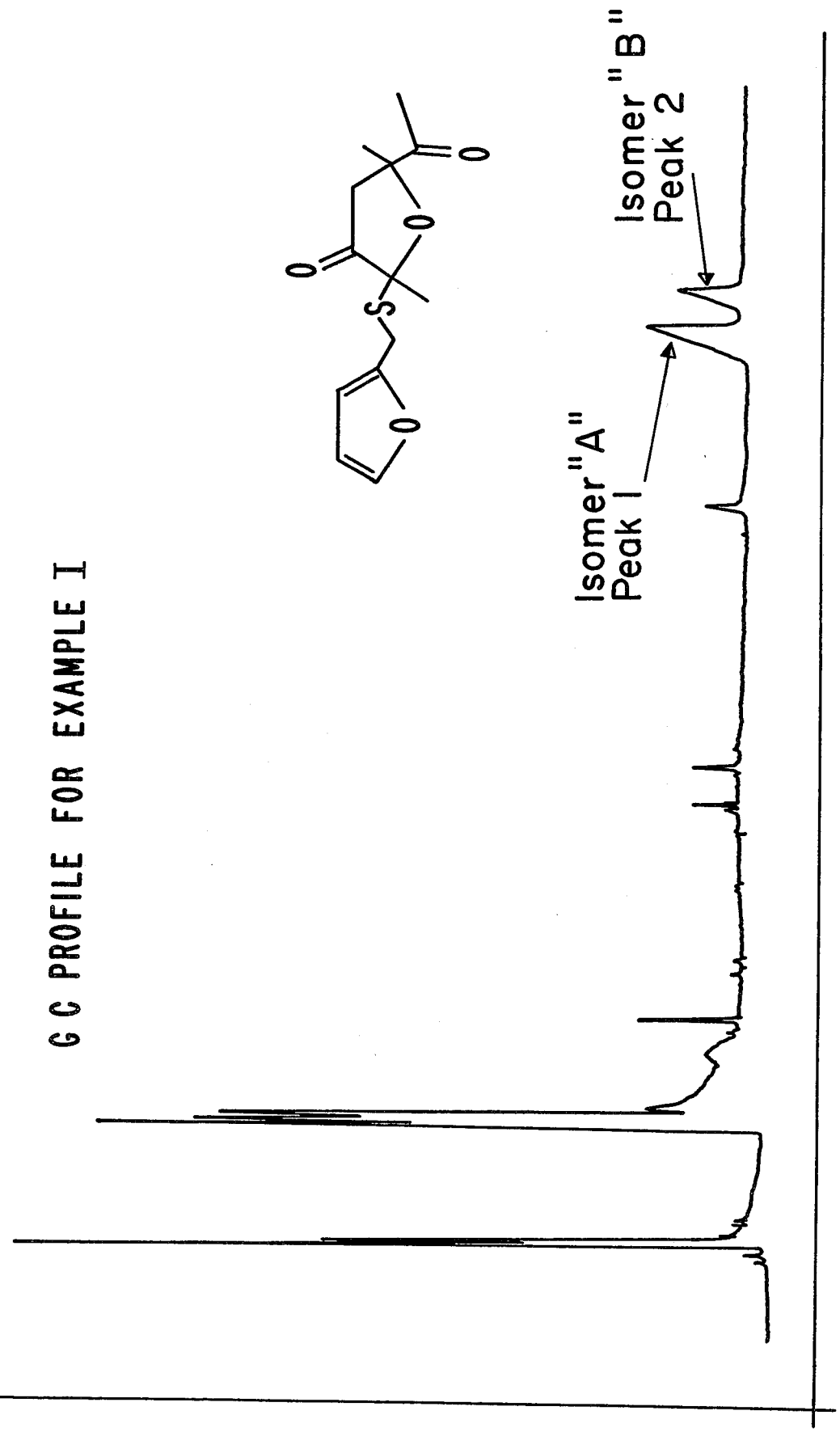

FIG. 5 represents the GC profile of the reaction product of Example I wherein one mole of diacetyl was reacted with one mole of furfuryl mercaptan.

Figure 6:
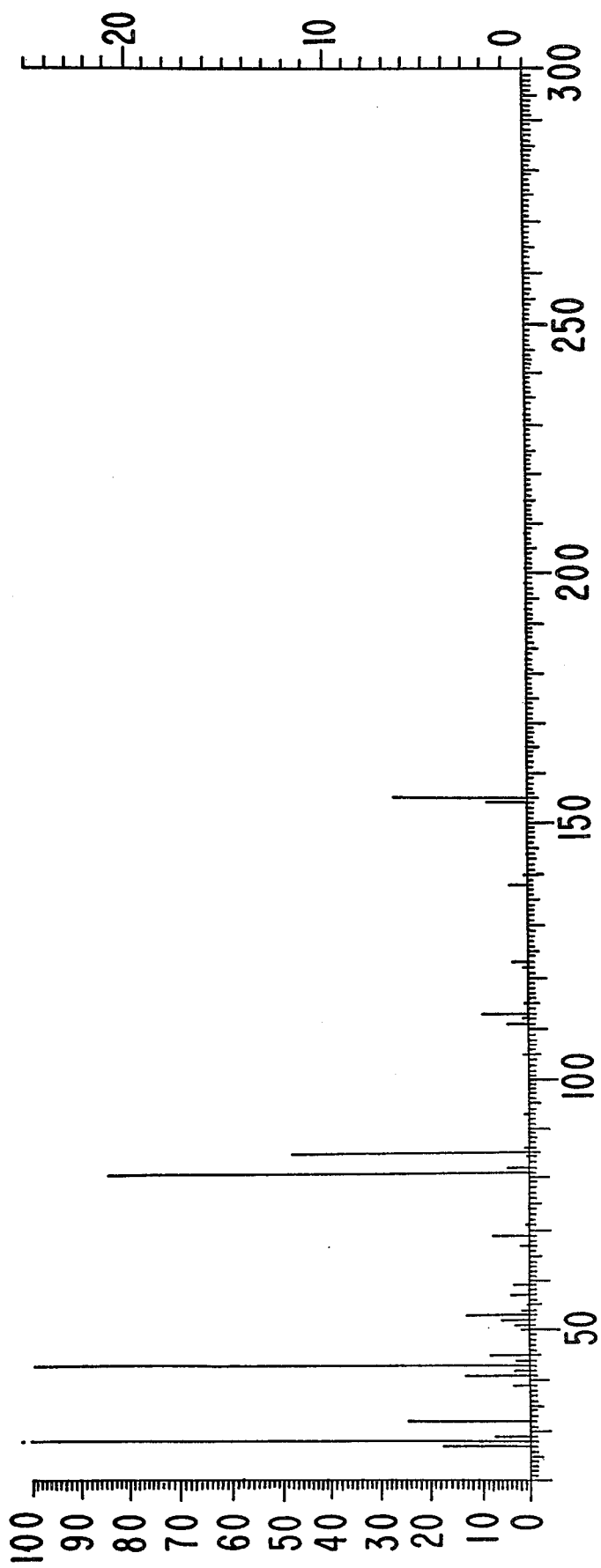

FIG. 6 represents the mass spectrum for isomer "A", peak 1, for the reaction product produced according to Example I.

Figure 7:
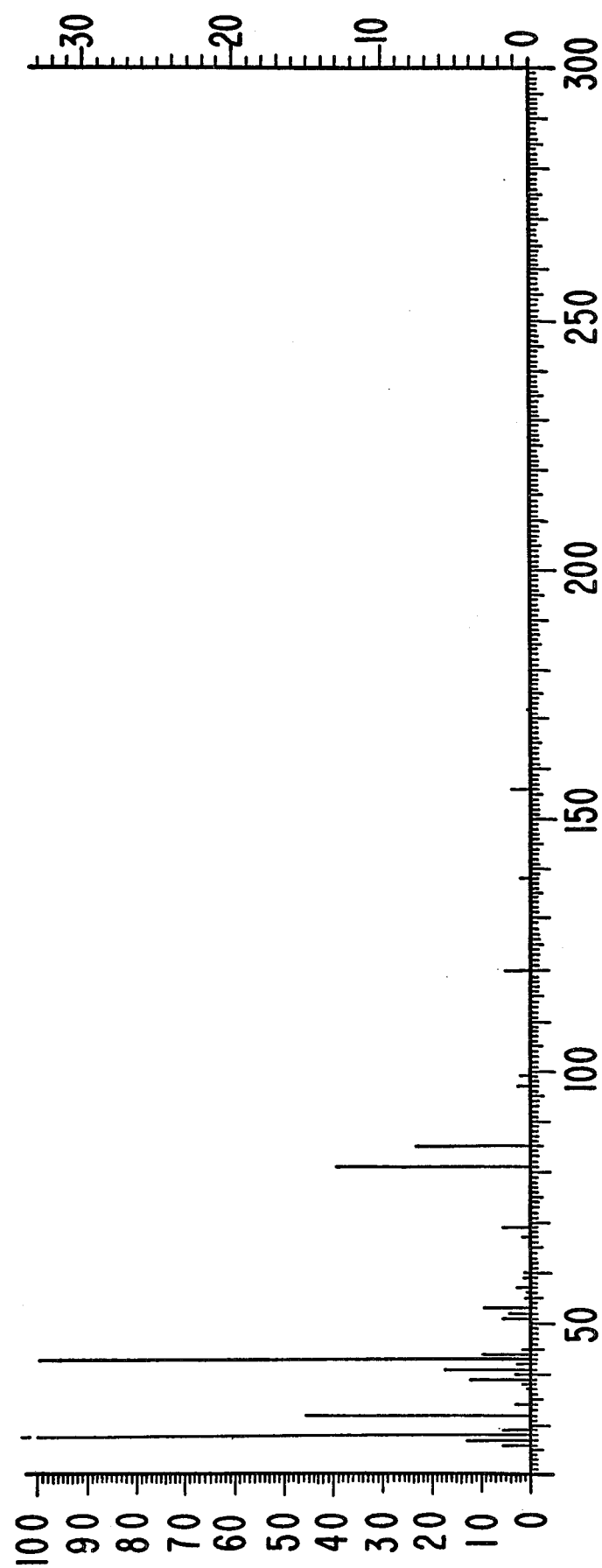

FIG. 7 represents the mass spectrum for isomer "B", peak 2, produced according to Example I.

FIG. 8 represents the GC profile for the reaction product of the diacetyl dimer with furfuryl mercaptan one hour and 52 minutes after addition of diacetyl dimer to the mixture of hydrochloric acid and furfuryl mercaptan as carried out according to Example II.

FIG. 9 represents the GC profile for the reaction product of diacetyl dimer with furfuryl mercaptan at that point in time after carrying out the reaction of diacetyl dimer with furfuryl mercaptan in the presence of hydrochloric acid for 6 hours and 20 minutes at 50°C. for 16 hours at 25° C. according to Example II.

THE INVENTION

It has now been discovered that novel solid and liquid foodstuff, chewing gum, medicinal product and toothpaste compositions and flavoring compositions therefor having coffee, roasted, cocoa-like, caramel-like, licorice and roasted almond aroma and flavor characteristics as well as novel tobacco and tobacco flavoring compositions and substitute tobacco and substitute tobacco flavoring compositions having sweet, caramel/coffee-like aromas and taste prior to and on smoking and nutty/-pyrazine-like aroma and flavor charcteristics prior to and on smoking with roasted nut-like nuances may be provided by the utilization of one or more 5-acyl-2-(furfurylthio)dihydro-2,5-dialkyl-3-[2H]furanones (either "cis" or "trans" isomers or mixtures of "cis" and "trans" isomers) having the generic formula:

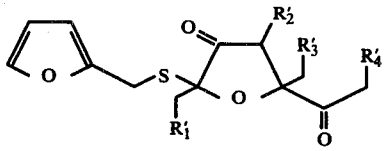

in foodstuffs, chewing gums, toothpastes, medicinal products, tobaccos and tobacco substitutes (wherein each of $R_1'$, $R_2'$, $R_3'$ and $R_4'$ are the same or different and each can be hydrogen or methyl).

The 5-acyl-2-(furfurylthio)dihydro-2,5-dialkyl-3-[2H]furanones useful as indicated supra may be produced preferably by one of two alternate routes of a process using one or more $C_4$-$C_6$ alpha, beta diketones and furfuryl mercaptan as reactants. A first route involves a reaction of one or more alpha, beta diketones having the generic structure:

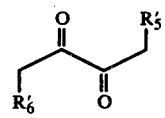

with furfuryl mercaptan to form one or more addition products having the generic structure:

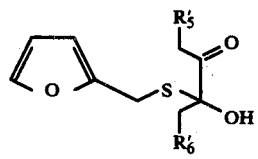

wherein $R_5'$ and $R_6'$ are the same or different and each represents hydrogen or methyl. When using one alpha, beta diketone in this reaction, two addition products are formed in the event that $R_5'$ and $R_6'$ are different; one wherein $R_5'$ is methyl and $R_6'$ is hydrogen and the other wherein $R_5'$ is hydrogen and $R_6'$ is methyl. When two or more different alpha, beta diketone compounds in this reaction two or more compounds are formed depending on (1) whether $R_5'$ and $R_6'$ are the same or different in each of the diketones and (2) the number of different diketones used in the mixture. The addition product(s) defines by the structure:

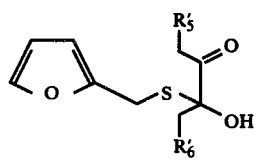

is (are) then reacted in this first route with one or more alpha, beta diketone(s) which may be the same as or different from the alpha, beta diketone reactants employed in the first reaction of this route having the structure:

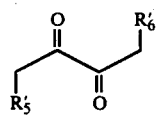

wherein a mixture of isomers (and in several cases a mixture of compounds) is produced defined by the generic structure:

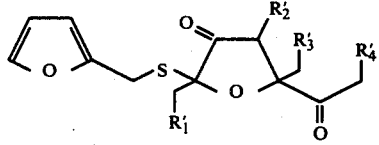

wherein $R_1'$, $R_2'$, $R_3'$ and $R_4'$ are the same or different and each represents hydrogen or methyl. Thus, in the case where one alpha, beta diketone is employed in each of the two reactions of this first route, a mixture of isomers is formed in the event that $R_5'$ and $R_6'$ are different in the case of one or both $C_4$-$C_6$ alpha, beta diketone reactants. Thus, in this first route, if $R_5'$ and $R_6'$ are different insofar as the diketone employed in the first reaction is concerned (e.g. hydrogen and methyl respectively) and if in the second reaction $R_5'$ and $R_6'$ of the alpha, beta diketone reactant having the structure:

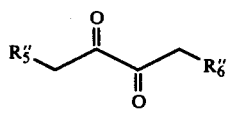

are the same (e.g. both hydrogen or both methyl, respectively) then the isomer mixture for the product having the structure:

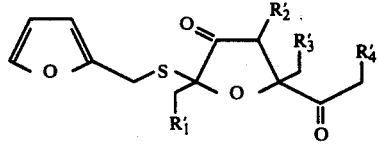

will be such that $R_3'$ and $R_4'$ are either both hydrogen or both methyl and $R_1'$ and $R_2'$ are such that one of the isomers is the compound wherein $R_1'$ is methyl and $R_2'$ is hydrogen and the other of the isomers is the compound where $R_2'$ is methyl and $R_1'$ is hydrogen. Furthermore, each of the aforesaid two isomers exists in 2 "geometric" forms a "cis" and a "trans" form having the structures, respectively:

-continued

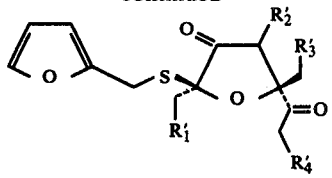

The foregoing reaction sequence of the first route is illustrated using the following two cases:

I. Where the first reaction employs the alpha, beta diketone, 2,3-pentanedione and the second reaction employed the alpha, beta diketone, 3,4-hexanedione:

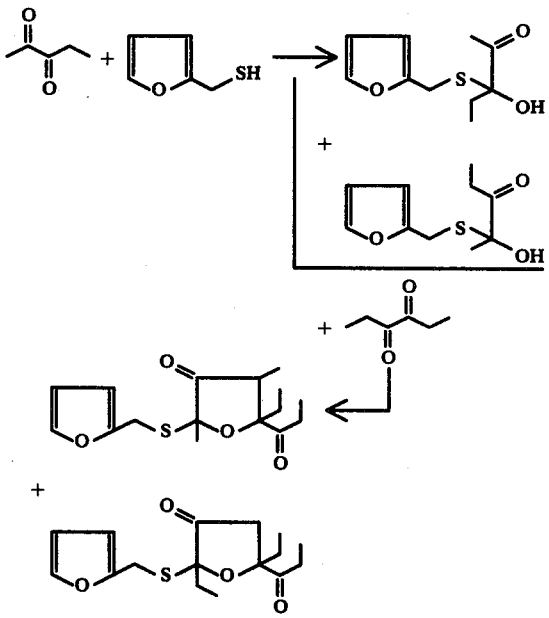

II. Where the first reaction employs a mixture of alpha, beta diketones, 2,3-pentanedione and 2,3-butanedione and the second reaction employs the alpha, beta diketone, 3,4-hexanedione.

-continued

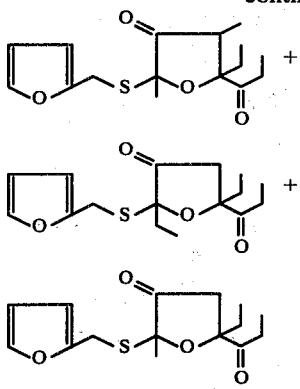

The second route usable for producing 5-acyl-2-(furfurylthio)dihydro-2,5-dialkyl-3-[2H] furanones having the structure:

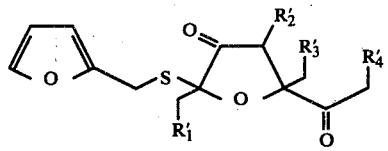

involves reacting one or more dimers of the $C_4$-$C_6$ alpha, beta diketone(s) which dimer(s) is (are) defined by the structure:

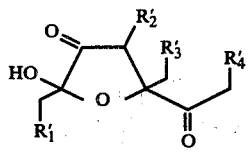

with furfuryl mercaptan having the structure:

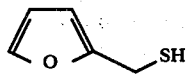

in the presence of an acid catalyst, preferably a mineral acid catalyst such as hydrochloric acid, phosphoric acid, para-toluene sulfonic acid or sulfuric acid. The $C_4$-$C_6$ alpha, beta diketone dimer substance can be a mixture of dimers resulting from dimerization of an unsymmetrical ketone or resulting from dimerization of two different ketones, each of which may be symmetrical or unsymmetrical or it can be a substantially pure dimer resulting from dimerization of a symmetrical alpha, beta diketone. Thus, and more specifically in the case of pure dimers having the structure:

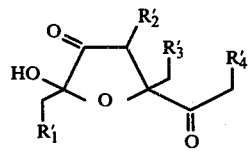

wherein $R_1'$, $R_2'$, $R_3'$ and $R_4'$ are the same or different and each represents hydrogen or methyl. Such a substantially pure dimer is formed from the $C_4$-$C_6$ alpha, beta diketone having the structure:

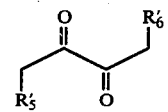

wherein $R_5'$ and $R_6'$ are the same; that is both represent hydrogen or both represent methyl. On the other hand, the $C_4$-$C_6$ alpha, beta diketone dimer substance (or composition) can be formed by dimerizing one or more $C_4$-$C_6$ alpha, beta diketones wherein in at least one of the diketones $R_5'$ and $R_6'$ are different for example $R_5'$ is hydrogen and $R_6'$ is methyl or $R_6'$ is hydrogen and $R_5'$ is methyl; in which case a mixture of dimers would be formed as a result of the dimerization reaction and wherein in at least one of the dimers formed $R_1'$ and $R_2'$ are different one of them being hydrogen and the other being methyl and $R_3'$ and $R_4'$ are different, one of them being hydrogen and the other of them being methyl. Still further, in the dimerization reaction where two different $C_4$-$C_6$ alpha, beta diketones are reacted (the reaction taking place in the presence of a basic material such as sodium hydroxide, potassium hydroxide, sodium carbonate and potassium carbonate), each of the diketones, individually, will dimerize and the different diketones will also dimerize with one another thereby forming up to 16 isomers, each isomer being in both a "cis" and "trans" form.

As a specific example, when the two alpha, beta diketones 2,3-pentanedione having the structure:

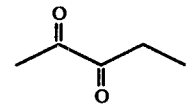

and 2,3-butanedione having the structure:

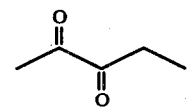

are reacted in the presence of base. The structures of the dimers formed are as follows:

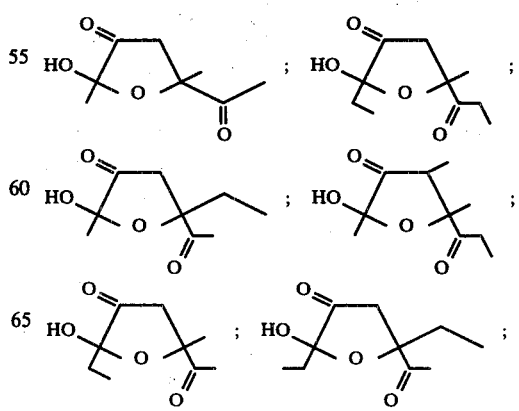

-continued

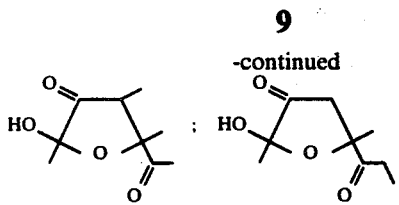

these dimers with furfuryl mercaptan according to the process of our invention.

The aforementioned two reaction sequences, the one using as starting materials furfuryl mercaptan and one or more $C_4$-$C_6$ alpha, beta diketones and the other using the dimer of the $C_4$-$C_6$ alpha, beta diketones and furfuryl mercaptan are set forth below:

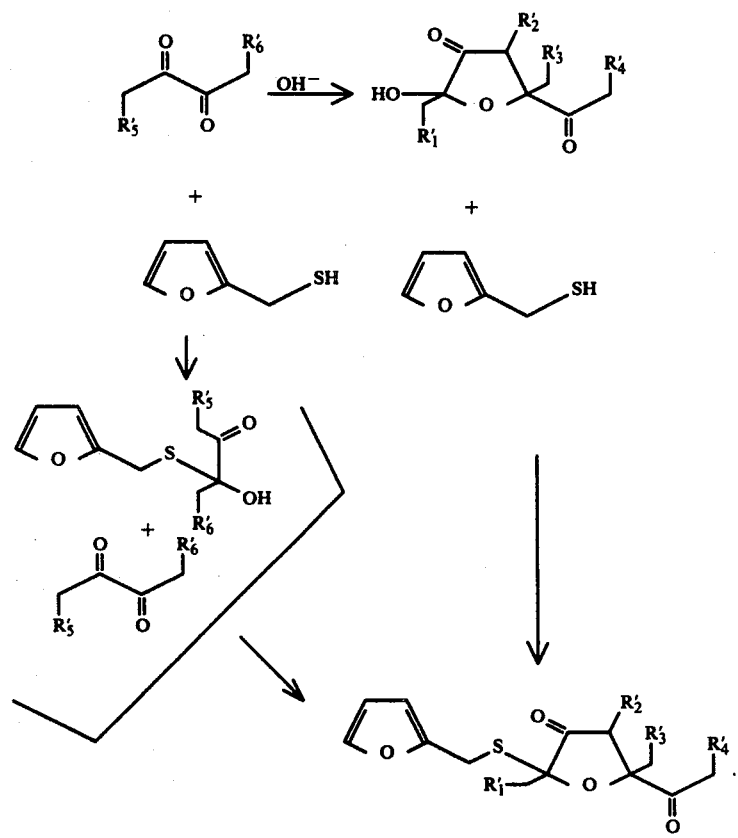

and the most practical and commercially feasible method of operation is to react the entire mixture of More specifically this is exemplified by the use of diacetyl or the diacetyl dimer and furfuryl mercaptan as set forth below:

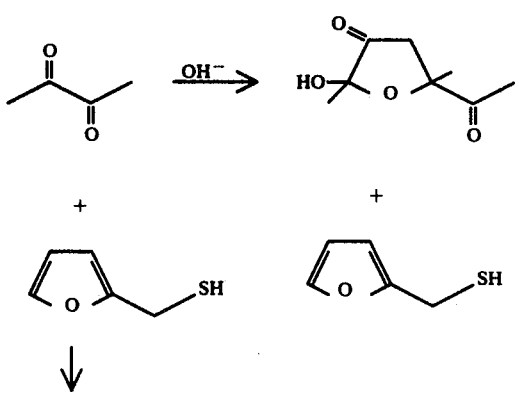

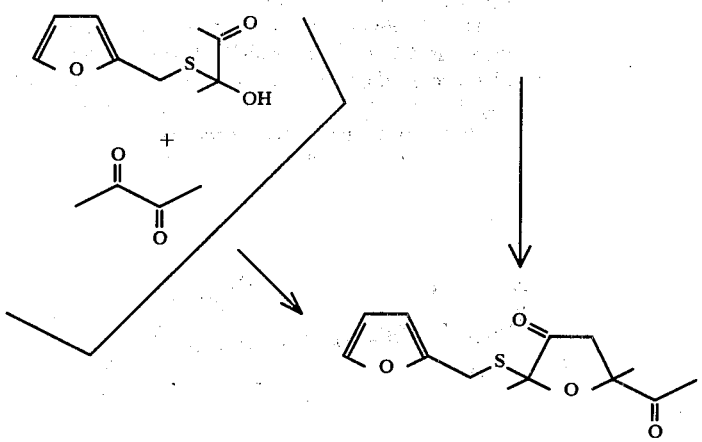

With reference to the first route as set forth above, the reaction of furfuryl mercaptan with the $C_4$-$C_6$ alpha, beta diketone (s) to form the intermediate having the structure:

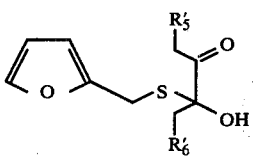

and subsequent reaction of said intermediate with the same or a different $C_4$-$C_6$ alpha, beta diketone. The mole ratio of $C_4$-$C_6$ alpha, beta diketone: furfuryl mercaptan is 2:1 up to about 10:1 with a preferred ratio range of from 2:1 up to 3:1. It is preferred in this first reaction sequence that the reaction is carried out under reflux condition at temperatures in the range of from about 100° C. up to about 150° C. for a period of time of from about 3 hours up to about 20 hours. Although the reaction may be carried out in the absence of a solvent, if a solvent is to be used it is preferred that said solvent can be easily removed at the end of the reaction and that the solvent have a boiling point such that the reaction temperature range is in the range of from about 110° C. up to 150° C. The reaction is conveniently carried out at atmospheric pressure, however higher than atmospheric pressures or subatmospheric pressures may be used depending upon the desired temperature of reaction and solvent (if any) used with the reactants. The temperatures and pressures of reaction are preferably the same for both stages (i) the preparation of the intermediate having the structure:

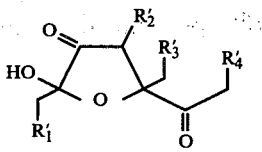

and (ii) the reaction of said intermediate with the additional mole of $C_4$-$C_6$ alpha, beta diketone.

Insofar as the second reaction sequence is concerned wherein one or more $C_4$-$C_6$ alpha, beta diketones is reacted to form one or more "dimers" defined by the generic structure:

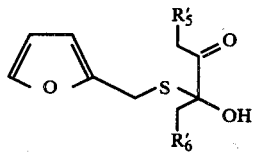

the said dimer(s) is (are) prepared by methods well known in the art (e.g. dimerization of the $C_4$-$C_6$ alpha, beta diketone in the presence of base). The reaction of the dimer with the furfuryl mercaptan preferably takes place in the presence of a solvent at temperatures in the range of from about 40° C. up to about 100° C. depending upon the solvents used and the time of reaction used. Preferably the solvent used is one wherein the reflux temperature of the reaction mass will be at temperatures of between 40° C. and 100° C. such as for example tetrahydrofuran. The pressure of reaction is preferably and most conveniently about one atmosphere, however, pressures of reaction of greater than one atmosphere or less than one atmosphere may be used without detrimentally affecting the yield of desired product. In order to avoid problems relating to the recovery of excess reactants it is preferable to use a mole ratio of $C_4$-$C_6$ alpha, beta diketone: furfuryl mercaptan of 1:1 although either of the reactants may be used in excess without detrimentally affecting the yield of reaction.

One or more of the 5-acyl-2-(furfurylthio)dihydro-2,5-dialkyl-3-[2H] furanones of our invention is capable of supplying and/or poentiating certain flavor and aroma notes usually lacking in many coffee, caramel, roasted nut and licorice flavors as well as tobacco flavors heretofore provided.

When the 5-acyl-2-(furfurylthio)dihydro-2,5-dialkyl-3-[2H]furanones of our invention are used as food flavor adjuvants the nature of the coingredients included with each of the said 5-acyl-2-(furfurylthio)dihydro-2,5-dialkyl-3-[2H]furanones in formulating the product composition will also serve to alter or augment the organoleptic characteristics of the ultimate foodstuff treated therewith.

As used herein in regard to foodstuff flavors and chewing gum flavors and medicinal product flavors, the terms "alter", "modify" and "augment" in their various forms mean "supplying or imparting flavor character or notes to otherwise bland, relatively tasteless substances or augmenting the existing flavor characteristics where a natural flavor is deficient in some regard or where a specific flavor composition containing several ingredients some of which may be natural is deficient in some regard or supplementing the existing flavor impression to modify its quality, character or taste".

The term "enhance" is used herein to mean the intensification of a flavor aroma characteristic or note without the modification of the quality thereof. Thus, "enhancement" of a flavor or aroma means that the enhancement agent does not add any additional flavor note.

As used herein the term "foodstuff" includes both solids and liquids which are ingestible materials which usually do, but need not, have nutritional value. Thus, foodstuffs include soups, convenience foods, beverages, dairy products, candies, vegetables, cereals, soft drinks, snacks and the like and in addition intended herein to mean petfoods.

As used herein the term "medicinal product" includes both solids and liquids which are ingestible non-toxic materials which have medicinal value such as cough syrups, cough drops, aspirin, vitamin, lozenges and chewable medicinal tablets.

The term "chewing gum" is intended to mean the composition which comprises a substantially water-insoluble, chewable plastic gum base such as chicle, or substitutes therefor, including jelutong, guttakay, rubber or certain comestible natural or synthetic resin or waxes. Incorporated with the gum base in admixture herewith by be plasticizers or softening agents, e.g., glycerine; and a flavoring composition which incorporates one or more of the 5-acyl-2-(furfurylthio)dihydro-2,5-dialkyl-3-[2H]furanones of our invention and, in addition, sweetening agents which may be sugars, including sucrose or dextrose and/or artificial sweeteners such as cyclamates or saccharin. Other optional ingredients may also be present.

Suitable substances for use herein as coingredients or "flavoring adjuvants" are well known in the art for such use, being extensively described in the relevant literature. It is a requirement that any such material be "ingestibly" acceptable, non-toxic and otherwise non-deleterious particularly from an organoleptic standpoint whereby the ultimate flavor and/or aroma of the consumable material used is not caused to have unacceptable aroma and taste nuances.

Those materials which in general may be characterized as "flavoring adjuvants" comprise broadly vehicles, stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxyanisole), butylated hydroxy toluene (2,6-di-tertiarybutyl-4-methyl phenol), propyl gallate and the like and sequestrants, e.g., citric acid.

Thickener compounds include carriers, binders, protective colloids, suspending agents, emulsifiers and the like, e.g., agaragar, carrageenan; cellulose and cellulose derivatives such as carboxymethyl cellulose and methyl cellulose; natural and synthetic gums such as gum arabic, gum tragacanth; gelatin, proteinaceous materials; lipids; carbohydrates; starches, pectins, and emulsifiers, e.g., mono-and diglycerides of fatty acids, skim milk powder, hexoses, pentoses, disaccharides, e.g., sucrose corn syrup and the like.

Surface active agents include emulsifying agents, e.g., fatty acids such as capric acid, caprylic acid, palmitic acid, myristic acid and the like, mono-and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate,, ammonium bicarbonate, ammonium phosphate, citric acid, lactic acid, vinegar and the like; colorants, e.g., carminic acid, cochineal, tumeric and curcuma and the like; firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include:

(i) Insofar as coffee flavors are concerned:

Hydrogen sulfide
Formaldehyde
Formic acid
Methanol
Methyl mercaptan
Carbon disulfide
Acetaldehyde
Acetic acid
Methyl formate
Ethanol
Dimethyl sulfide
Dimethyl disulfide
Acrylonitrile
Acrolein
Propanal
Acetone
Propionic acid
Acetol
Methyl acetate
Ethyl formate
Methyl ethyl sulfide
Methyl ethyl disulfide
Furan
Thiophene
Crotonolactone
Pyrazine
3-Butene nitrile
Pyrrole
Methyl vinyl ketone
Diacetyl
Butyrolactone
Crotonic acid
i-Butanal
Butanal
Butanone
i-Butyric acid
Acetoin
Ethyl acetate
Furfural
Pyridine
2-Pyrrolaldehyde
2-Methylfuran Furfuryl alcohol
2-Methylpyrazine
N-Methylpyrrole
Isoprene
Pentadiene
Cyclopentanone
Pentane-2,3-dione
2-Methyltetrahydrofuran-3-one
Senecioic acid
Acetylacetone
Acetol acetate
2-Methylbutanal
3-Methylbutanal
Valeraldehyde
2-Hydroxy-3-pentanone
3-Hydroxy-2-pentanone
i-Valeric acid
2-Methylbutyric acid
Phenol
5-Methylfurfural
2-Acetylfuran
Furfuryl formate
Dimethylmaleic anhydride
2-Methyl-3-hydroxy-γ-pyrone
2-Acetylthiophene
3-Methylpyridine
2-Acetylpyrrole
N-Methylpyrrole-2-aldehyde
5-Methylpyrrole-2-aldehyde
2,5-Dimethylfuran
3-Methylcyclopentane-1,2-dione
2,3-Dimethylpyrazine
2,5-Dimethylpyrazine
2,6-Dimethylpyrazine
Furfuryl methyl sulfide
2-Methyl-3-ethylacrolein
1-(2'-furyl)-propane-1,2-dione
Methyl nicotinate
Toluene
m-Cresol
Guaiacol
5-Methyl-2-acetylfuran
Furfuryl acetate
Methyl ethyl maleic anhydride
2-Propionylpyrrole
N-Methyl-2-acetylpyrrole
N-Methyl-5-methylpyrrole-2-aldehyde
2-Propylfuran
3,4-Dimethylcyclopentane-1,2-dione
3,5-Dimethylcyclopentane-1,2-dione
3-Ethylcyclopentane-1,2-dione
3-Methylcyclohexane-1,2-dione
2,3-Dihydroxyacetophenone 1-(2'-Furyl)-butane-1,2-dione
1-[(5'-Methyl)-2'furyl]-propane-1,2-dione 2-Butylfuran
2,2'-Difurylmethane
N-Furfuryl-2-pyrrole
4-Vinylguaiacol
4-Ethylguaiacol Insofar as cocoa flavors are concerned, aliphatic compounds such as:

Acetaldehyde
Acetic acid
Acetone
Acetoxyacetone
Acrolein
2-Aminobutane
n-Amyl acetate
n-Amyl alcohol
Amyl butyrate
Amyl propionate 2,3-Butandiol
2,3-Butanedione
2-Butanon-3-ol
n-Butyl acetate
n-Butyraldehyde
n-Butyric acid
Caproic acid
Caprylic acid
Citronellal
Crotonaldehyde
Dimethylamine
Ethanol
Ethyl acetate
Ethylamine
Ethyl caproate
Ethyl propionate
Formic acid
Geraniol
3-Heptadecanone
1-Hexanol
Hexyl butyrate
Hexyl propionate
Isoamyl acetate
Isoamylamine
Isobutanol
Isobutyl acetate
Isobutylamine
Isobutyraldehyde
Isovaleraldehyde
Linalool
Linalyl acetate
Methanol
Methyl acetate
Methylamine
α-Methylbutyric acid
Methyl disulfide
2-Methyl-2-hepten-6-one
Methyl sulfide
Methyl trisulfide
2,4-Octadien-1-ol
1-Octen-3-ol
Pelargonic acid
2,3-Pentandione
2-Pentyl acetate
1-Propanol
2-Propanol
Propionaldehyde
Propionic acid
1-Propyl acetate
2-Propyl acetate
Propyl trisulfide
Triethylamine
Trimethylamine
n-Valeric acid;

Alicyclic compounds such as:

3-Methyl-1,2-cyclopentanedione

Aromatic compounds such as:

Acetophenone
Benzaldehyde
Benzene

Benzonitrile
Benzyl alcohol
Cresol
3,4-Dihydroxybenzoic acid
6,7-Dihydroxycoumarin
Ethyl benzoate
p-Ethylphenol
Ethyl phenylacetate
Eugenol
Guaiacol
o-Hydroxyacetophenone
p-Hydroxybenzoic acid
p-Hydroxycinnamic acid
4-Hydroxy-3,5-dimethoxy-benzoic acid
4-Hydroxy-3-methoxy-benzoic acid
4-Hydroxy-3-methoxy-cinnamic acid
o-Hydroxyphenylacetic acid
p-Hydroxyphenylacetic acid
p-Methoxybenzoic acid
4-Methylguaiacol
Methyl phenylacetate
Phenol
Phenyl acetate
Phenylacetic acid
Phenylacetic aldehyde
2-Phenylethyl acetate
1-Phenylethyl alcohol
2-Phenylethyl alcohol
2-Phenylethylamine
2-Phenyl-2-propanol
Toluene Heterocyclic compounds such as:

γ-Butyrolactone
γ-Caprolactone
Furan
Furfural
Furfuryl acetate
Furfuryl alcohol
2-Furyl methylacetone
Maltol
α-Methyl-γ-butyrolactone
2-Methylfuran
Methyl-5-methylfurfuryl sulfide
2-Methyl-3-tetrahydrofuranone
γ-Valerolactone
cis-2-Vinyl-2-methyl-5-(1-hydroxy-1-methylethyl)-tetrahydrofuran Pyrrole compounds such as:

2-Acetylpyrrole
2-Formylpyrrole
1-Methyl-2-formylpyrrole
5-Methyl-2-formylpyrrole
Pyrrole Pyrazine compounds such as:

2,5-Dimethyl-6-ethylpyrazine
2,6-Dimethyl-3-ethylpyrazine
2,3-Dimethylpyrazine
2,5-Dimethylpyrazine
2,6-Dimethylpyrazine
2-Ethyl-5-methylpyrazine
2-Ethyl-6-methylpyrazine
Methylpyrazine
Tetramethylpyrazine
Trimethylpyrazine
2-Ethyl-3,5,6-trimethylpyrazine
3-Isoamyl-2,5-dimethylpyrazine
5-Isoamyl-2,3-dimethylpyrazine
2-Isoamyl-3,5,6-trimethyl-pyrazine
Isopropyl dimethylpyrazine Hydrocarbons such as:

Dimethyl naphthalene
Dodecane
Methyl diphenyl
Methyl naphthalene
Myrcene
Naphthalene
Octadecane
Tetradecane
Tetramethyl naphthalene
Tridecane
Trimethyl naphthalene
Undecane Alcohols and Ketoalcohols such as:

Acetoin
2-Heptanol
Linalool
1-Pentanol

Aldehydes such as:

Isopentanal
2-Methylbutanal

Ketones such as:

2-Heptanone
2Methyl-2-hepten-6-one
2-Octanone
2-Undecanone

Esters and lactones such as:

Benzyl acetate
Ethyl caprate
Ethyl caproate
Ethyl caprylate
Ethyl cinnamate
Ethyl laurate
Ethyl myristate
Isoamyl acetate
γ-Nonalactone Acids such as:

Isovaleric acid
2-Methylbutyric acid

Phenols such as:

2-Methoxy-4-methylphenol

Insofar as licorice flavor is concerned:

Lavender essential oil
Clary sage essential oil
Rosemary essential oil

Thyme essential oil
Fennel essential oil
Mint essential oil
Angelica essential oil
Anise essential oil
Lemon essential oil
Wormwood essential oil
Cinnamon essential oil The specific flavoring adjuvant selected for use may be either solid or liquid depending upon the desired physical form of the ultimate product, i.e., foodstuff, whether simulated or natural, and should, in any event, (i) be organoleptically compatible with the 5-acyl-2-(furfurylthio)dihydro-2,5-dialkyl-3-[2H]furanone or furanones of our invention by not covering or spoiling the organoleptic properties (aroma and/or taste) thereof; (ii) be non-reactive with the 5-acyl-2-(furfurylthio) dihydro-2,5-dialkyl-3-[2H]furanone or furanones of our invention and (iii) be capable of providing an environment in which the 5-acyl-2-(furfurylthio)dihydro-2,5-dialkyl-3-[2H]furanone or furanones of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of 5-acyl-2-(furfurylthio)dihydro-2,5-dialkyl-3-[2H]furanone or furanones employed in a particular instance can vary over a relatively wide range, depending upon the desired organoleptic effects to be achieved. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition whether foodstuff per se, chewing gum per se, medicinal product per se, toothpaste per se, or the flavoring composition itself.

The use of insufficient quantities of 5-acyl-2-(furfurylthio) dihydro-2,5-dialkyl-3-[2H]furanone or furanones will, of course, substantially vitiate any possibility of obtaining the desired results while excess quantities of 5-acyl-2-(furfurylthio) dihydro-2,5-dialkyl-3-[2H]furanone or furanones prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of 5-acyl-2-(furfurylthio)dihydro-2,5-dialkyl-3-[2H]furanone or furanones (in combination) ranging from a small but effected amount, e.g., 0.01 parts per million up to about 100 parts per million based on total composition are suitable. Concentrations in excess of the maximum quantity stated are not normally recommended, since they fail to provide commensurate enhancement or augmentation of organoleptic properties. In those instances, wherein the 5-acyl-2-(furfurylthio) dihydro-2,5-dialkyl-3-[2H]furanone or furanones are added to the foodstuff as an integral component of a flavoring composition, it is, of course, essential that the total quantity of flavoring composition employed be sufficient to yield an effective 5-acyl-2-(furfurylthio) dihydro-2,5-dialkyl-3-[2H]furanone concentration in the foodstuff product.

Food flavoring compositions prepared in accordance with the present invention preferably contain the 5-acyl-2-(furfurylthio) dihydro-2,5-dialkyl-3-[2H]furanone or furanones (in combination) in concentrations ranging from about 0.05% up to about 20% by weight based on the total weight of said flavoring composition.

The compositions described herein can be prepared according to conventional techniques well known as typified by cake batters, ice creams, liquers and soft drinks and be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the 5-acyl-2-(furfurylthio) dihydro-2,5-dialkyl-3-[2H]furanone or furanones with, for example, gum arabic, gum tragacanth, carrageenan and the like, and thereafter spray-drying the resultant mixture whereby to obtain the particulate solid product. Pre-prepared flavor mixes in powder form, e.g., cocoa-flavored powder mixes and coffee flavored powder mixes are obtained by mixing the dried solid components, e.g., starch, sugar and the like and an 5-acyl-2-(furfurylthio)dihydro-2,5-dialkyl-3-[2H] furanone or furanones in a dry blender until the requisite degree of uniformity is achieved.

It is presently preferred to combine with the 5-acyl-2-(furfurylthio)dihydro-2,5dialkyl-3-[2H]furanone or furanones of our invention the following adjuvants:

Diacetyl
Benzaldehyde
Furfural
Furfuryl propionate
Trimethyl pyrazine
2,6-Dimethoxyphenol
Pyruvic acid
Furfuryl mercaptan
Furfuryl acetate An additional aspect of our invention provides an organoleptically improved smoking tobacco product and additives therefor, as well as methods of making the same which overcome specific problems heretofore encountered in which specific desired "sweet, caramel/coffee-like, nutty, and roasted nutty" flavor characteristics of natural tobacco are created or enhanced and may be readily controlled and maintained at the desired uniform level regardless of variations in the tobacco components of the blend.

This invention further provides improved tobacco additives and methods whereby various desirable natural aromatic tobacco flavoring characteristics with sweet, caramelcoffee, nutty and roasted nutty notes may be imparted to smoking tobacco products and may be readily varied and controlled to produce the desired uniform flavor characteristics.

In carrying out this aspect of our invention, we add to smoking tobacco materials or a suitable substitute therefor (e.g., dried lettuce leaves) an aroma and flavor additive containing as an active ingredient at least one 5-acyl-2-(furfurylthio)dihydro-2,5dialkyl-3-[2H]furanone or a combination of 5-acyl-2-(furfurylthio)dihydro-2,5-dialkyl-3-[2H]furanones.

In addition to the 5-acyl-2-(furfurylthio)dihydro-2,5-dialkyl-3-[2H]furanone or furanones of our invention other flavoring and aroma additives may be added to the smoking tobacco material or substitutes therefor either separately or in admixture with the 5-acyl-2-(furfurylthio) dihydro-2,5-dialkyl-3-[2H]furanone or furanones as follows:

(i) Synthetic materials:
Beta-ethyl-cinnamaldehyde;
Beta-cyclohomocitral;
Eugenol;
Dipentene;
Damascenone;
Damascone;
Maltol;
Ethyl Maltol;
Delta undecalactone;
Delta decalactone;
Benzaldehyde;
Amyl acetate;
Ethyl butyrate;
Ethyl valerate;
Ethyl acetate;
2-Hexenol-1
2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5-8a-tetramethyl-1-(2-hydroxyethyl)-decahydronaphthalene;
Dodecahydro-3a,6,6,9a-tetramethyl naphtho-[2,1,b]-furan;
4-hydroxy hexanoic acid, gamma lactone; Polyisoprenoid hydrocarbons defined in Example V of U.S. Pat. No. 3,589,372 issued on June 29, 1971.

(ii) Natural Oils:
Celery seed oil;
Coffee extract;
Bergamot oil;
Cocoa extract;
Nutmeg oil;
Origanum oil An aroma and flavoring concentrate containing a 5-acyl-2-(furfurylthio) dihydro-2,5-dialkyl-3-[2H]furanone or furanones and, if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as enhancement or the inparting of natural and/or sweet, coffee/caramel, nutty or roasted nutty notes, we have found that satisfactory notes are obtained if the proportion by weight of the sum total of 5-acyl-2-(furfurylthio) dihydro-2,5-dialkyl-3-[2H]furanone or furanones to smoking tobacco material is between 10 and 1,500 ppm (0.001–0.15%) of the active ingredients to the smoking tobacco material. We have further found that satisfactory results are obtained if the proportion by weight of the sum total of 5-acyl-2-(furfurylthio) dihydro-2,5-dialkyl-3-[2H]furanone or furanones used to flavoring material is between 2,500 and 15,000 ppm (0.25%–1.5%).

Any convenient method for incorporating the 5-acyl-2-(furfurylthio) dihydro-2,5-dialkyl-3-[2H]furanone or furanones into the tobacco product may be employed. Thus, the 5-acyl-2-(furfurylthio) dihydro-2,5-dialkyl-3-[2H] furanone or furanones taken alone or along with other flavoring additives may be dissolved in a suitable solvent such as ethanol, diethyl ether, tetrahydrofuran and/or volatile organic solvents and the resulting solution may either be spread on the cured, cased and blended tobacco material or the tobacco material may be dipped into such solution. Under certain circumstances, a solution of the 5-acyl-2-(furfurylthio) dihydro-2,5-dialkyl-3-[2H] furanone or furanones taken alone or taken further together with other flavoring additives as set forth above, may be applied by means of a suitable applicator such as a brush or roller on the paper or leaf wrapper for the smoking product, or it may be applied to the filter by either spraying, or dipping, or coating.

Furthermore, it will be apparent that only a portion of the tobacco or substitute therefor need be treated and the thus treated tobacco may be blended with other tobaccos before the ultimate tobacco product is formed. In such cases, the tobacco treated may have the 5-acryl-2-(furfurylthio)dihydro-2,5-dialkyl-3-[2H]furanone or furanones in excess of the amounts of concentrations above indicated so that when blended with other tobaccos, the final product will have the percentage within the indicated range.

In accordance with one specific example of our invention, an aged, cured and shredded domestic burley tobacco is sprayed with a 20% ethyl alcohol solution of 5-acyl-2-(furfurylthio)dihydro-2,5-dimethyl-3]2H]furanone (mixture of "cis" and "trans" isomers produced according to Example II, infra) in an amount to provide a tobacco composition containing 50 ppm by weight of 5-acyl-2-(furfurylthio)dihydro-2,5-dimethyl-3[2H]furanone on a dry basis. Thereafter, the alcohol is removed by evaporation and the tobacco is manufactured into cigarettes by the usual techniques. The cigarette when treated as indicated has a desired and pleasing aroma which is detectable in the main and side streams when the cigarette is smoked. This aroma is described as being sweeter, more aromatic and having sweet, caramel/coffee-like, nutty/pyrazine-like and roasted nutty-like aromas and tastes.

While our invention is particularly useful in the manufacture of smoking tobacco, such as cigarette tobacco, cigar tobacco and pipe tobacco, other tobacco products formed from sheeted tobacco dust or fines may also be used. Likewise the 5-acyl-2-(furfurylthio)dihydro-2,5-dialkyl-3-[2H]furanone or furanones of our invention can be incorporated with materials such as filter tip materials, seam paste, packaging materials and the like which are used along with tobacco to form a product adapted for smoking. Furthermore, the 5-acyl-2-(furfurylthio)dihydro-2,5-dialkyl-3-[2H]furanone or furanones can be added to certain tobacco substitutes of natural or synthetic origin (e.g., dried lettuce leaves) and, accordingly, by the term "tobacco" as used throughout this specification is meant any composition intended for human consumption by smoking or otherwise, whether composed of tobacco plant parts or substitute materials or both.

The following examples serve to illustrate techniques for practicing our invention. It will be understood that these examples are illustrative and that the invention is to be considered restricted thereto only as indicated in the appended claims.

All parts and percentages given herein are by weight unless otherwise specified.

EXAMPLE I

PREPARATION OF 5-ACETYL-2-(FURFURYLTHIO) DIHYDRO-2,5-DIMETHYL-3[2H]FURANONE BY REACTION OF DIACETYL WITH FURFURYL MERCAPTAN FOLLOWED BY ADDITIONAL REACTION OF THE RESULTING PRODUCT WITH DIACETYL

Reaction:

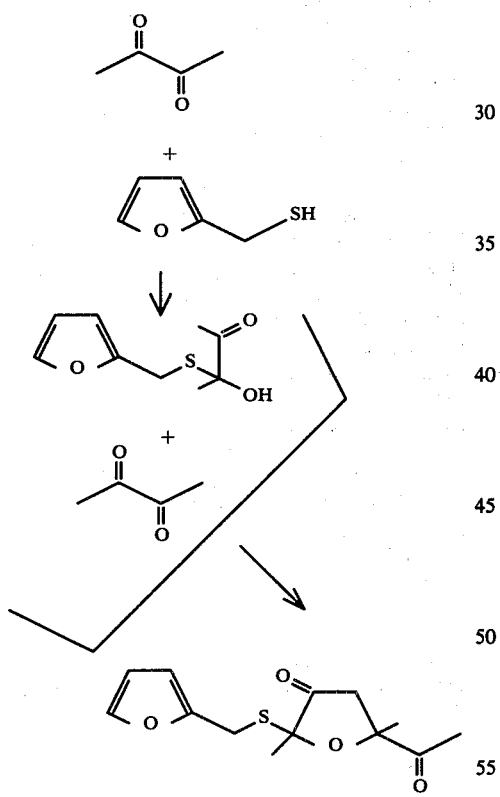

Into a 250 ml three-necked flask equipped with dual pass condenser, caustic safety trap and cold water circulating cooler is placed the following materials.

Furfuryl mercaptan: 122 grams (1.070 moles)
Diacetyl: 92.035 grams (1.065 moles) the reaction mass is then refluxed for a period of six hours at 118° C., following reflux the reaction mass is allowed to "age" for approximately three weeks.

The resulting reaction product is then analyzed by direct injection on a 400 ft. x 0.032" (I.D.) SE-30 glass capillary mounted on a Varian MAT III GC-MS instrument. The following results are obtained:

| Substance | Percent Composition |
|---|---|
| Diacetyl | 37 |
| Furfuryl mercaptan | 49 |
| Phenylacetaldehyde | 0.7 |
| Furfurylether | 0.2 |
| Difurfurylsulfide | 0.6 |
| Difurfuryldisulfide | 0.9 |
| 5-Acetyl-2-(furfurylthio) dihdyro-2,5-dimethyl-3-[2H]-furanone (cis or trans isomer) | 6.9 |
| 5-Acetyl-2-(furfurylthio) dihydro-2,5-dimethyl-3-[2H]-furanone (trans or cis isomer) | 3.2 |

The two isomers of 5-acetyl-2-(furfurylthio)dihydro-2,5-dimethyl-3-[2H]-furanone were fully characterized following their enrichment on 5% deactivated silica gel column eluted with 20% diethyl ether in isopentane. Based upon high resultion mass spectra, NMR and IR the compounds are determined to have the structure:

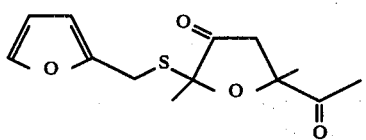

and each represents one of the isomers:

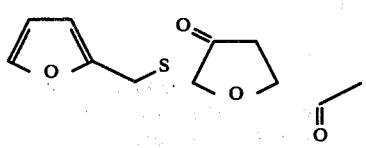

and

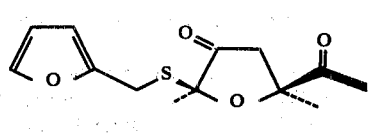

These conclusions are further supported by the chemistry involved in the synthesis set forth in Example II, infra.

Figure 1:
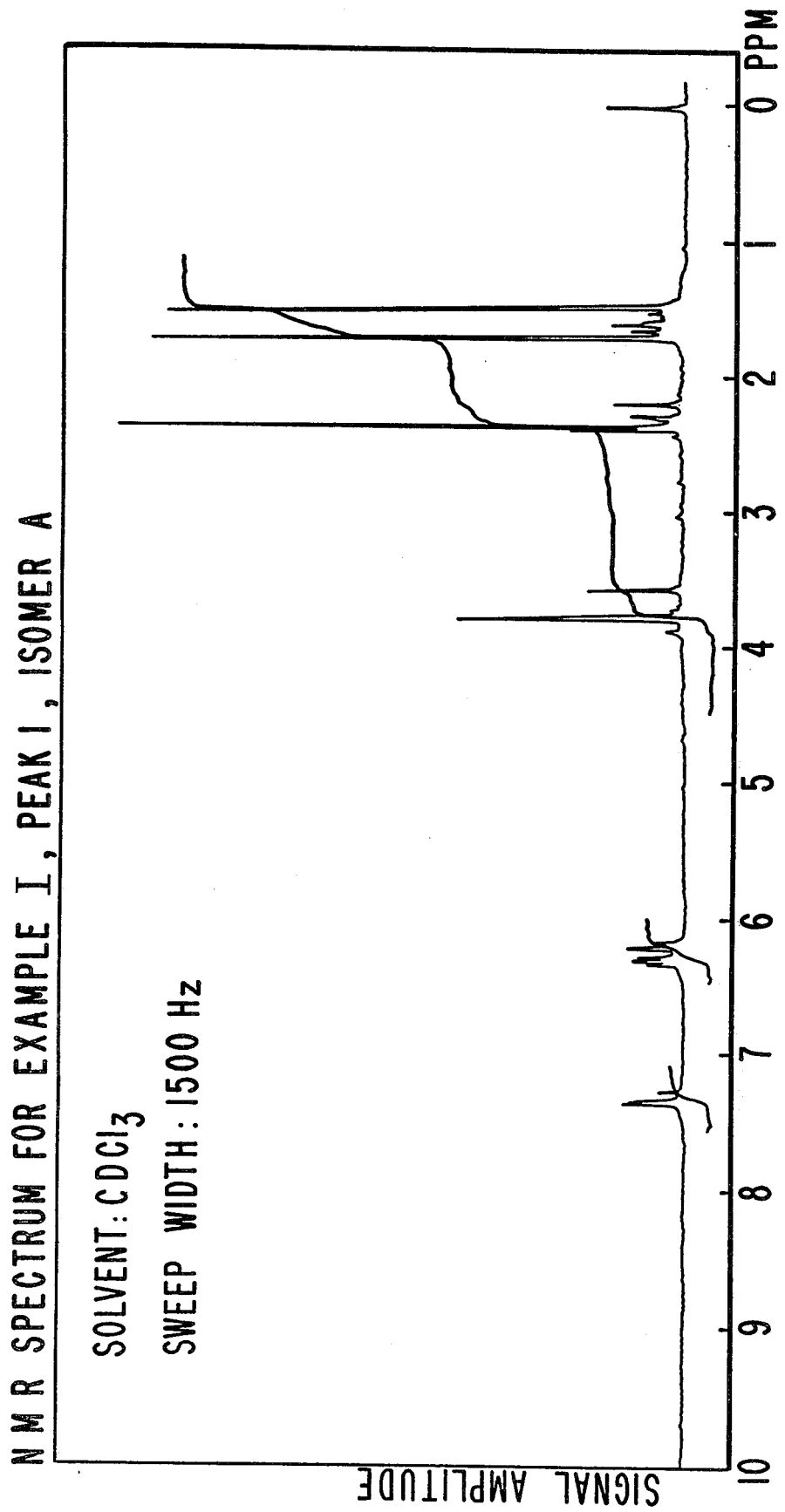
FIG. 1 represents the NMR spectrum for isomer "A", peak 1, produced according to the process of Example I and is the spectrum for the compound having one of the structures.

FIG. 1 represents the NMR spectrum for one of the isomers having the structures:

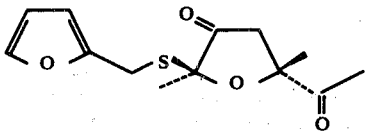

or

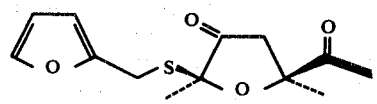

represented as isomer "A" which is peak "1" of the GC profile of FIG. 5. The NMR spectrum gives rise to the following NMR Analysis:

| δ | Interpretation | |
|---|---|---|
| 1.50 ppm (s) | CH₃—C(O—)(C=O)— | 3H |
| 1.70 (s) | CH₃—C(O=C—)(O—)(S) | 3H |
| 2.40 (s) | CH₃—C(=O)— | 3H |
| 3.80 (s) | C=C—CH₂—S— | 2H |
| 3.70 & 2.30 (AB) | —CH₂—C(=O)— | 2H |
| 6.26 (m) | furan protons | 2H |
| 7.38 (m) | furan protons | 1H |

FIG. 2 represents the NMR spectrum for the second isomer having one of the structures:

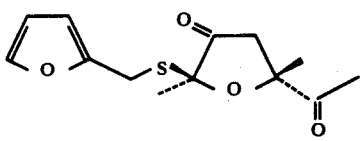

or

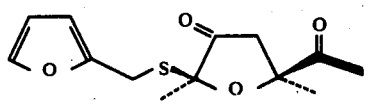

identified as isomer "B" which is peak "2" of the GC profile set forth in FIG. 5. The NMR spectrum gives rise to the following NMR Analysis:

| δ | Interpretation | |
|---|---|---|
| 1.63 ppm (s) | CH₃—C—C(=O)— | 3H |
| 1.70 (s) | CH₃—C(O=C—)(O—)(S) | 3H |
| 2.84 (AB) | —CH₂—C(=O)— | 2H |
| 2.98 (s) | C=C—CH₂—S— | 2H |
| 6.28 (m) | furan protons | 2H |
| 7.36 (m) | furan protons | 1H |

FIG. 3 represents the infrared spectrum for one of the isomers:

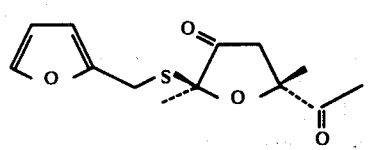

or

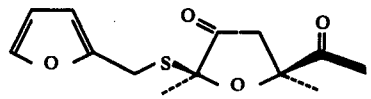

designated as isomer "A" which is peak "1" from the GC profile of FIG. 5. The infrared spectrum gives rise to the following peaks:

| Isomer "A" |
|---|
| 13.40 microns |
| 10.60 |
| 10.40 |
| 9.80 |
| 9.10 |
| 8.90 |
| 8.60 |
| 5.80 |
| 5.70 |

FIG. 4 represents the infrared spectrum for one of the isomers having one of the structures:

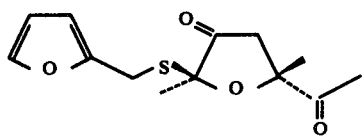

or

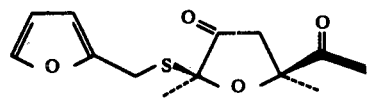

designated as isomer "B" which is peak "2" from the GC profile of FIG. 5. The infrared spectrum gives rise to the following infrared analysis:

| Isomer "B" |
|---|
| 13.35 microns |
| 10.60 |
| 9.80 |
| 9.10 |
| 8.65 |
| 7.30 |
| 7.20 |
| 5.80 |
| 5.70 |

FIG. 5 represents the GC profile for the reaction product of this example.

FIG. 6 represents the mass spectrum for isomer "A", peak "1".

FIG. 7 represents the mass spectrum for isomer "B", peak "2".

EXAMPLE II

Preparation of 5-Acetyl-2-Furfurylthiodihydro-2,5-Dimethyl-3,2H-Furanone According to the Reaction of Furfuryl Mercaptan and the Diacetyl Dimer Reaction:

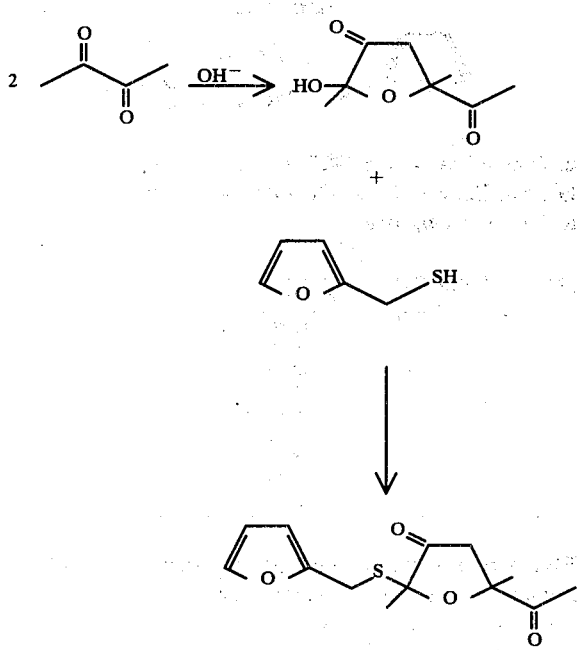

Into a 5 liter reactor equipped with reflux condenser, stirrer and cooling bath is added the following ingredients:

Diacetyl: 320 grams
Water: 3,200 ml the reaction mass is cooled to 3° C. at which point a solution of 54.4 grams of potassium hydroxide and 1,600 ml of water is added over a period of 20 minutes. 85 grams of 50% sulfuric acid is then added to the reaction mixture bringing the pH to 5.

The reaction mass is then saturated with 1600 grams of sodium chloride and then extracted with four 200 ml portions of methylene dichloride. The reaction mass is then dried over anhydrous sodium sulphate and stripped of solvent. The resulting product is then distilled through a 6" Vigreaux column followed by redistillation yielding the diacetyl dimer.

Into a 250 ml reaction flask equipped with reflux condenser, stirrer, thermometer and heating mantle is placed 20 grams (17.7 ml) of furfuryl mercaptan. 10 ml tetrahydrofuran and ½ ml concentrated HCl is then added. The reaction mass is heated to 50° C. and, over a 10 minute period, 30 grams of diacetyl dimer prepared as above in 20 grams of tetrahydrofuran is added. 20 ml tetrahydrofuran additional used to rinse the addition flask is then added.

The reaction mass is then stirred for 5 hours at 50°C. with GC samples taken each hour.

The resulting material is labeled "Batch #1".

Into another 250 ml flask equipped with stirrer, therommometer, reflux condenser and heating mantle is placed 1.7 grams of the diacetyl dimer prepared as above, 4 ml tetrahydrofuran and 1.3 grams (1 ml) of furfuryl mercaptan. Reaction mass is stirred for a period of 2 hours at which time 2 drops of concentrated hydrochloric acid is added. The reaction mass is then heated to 50°C. and stirred at 50°-52° C. for a period of one hour.

This last prepared material is labeled "Batch #2".

Batch 1 and Batch 2 are combined and to the combined batch is added 20 ml saturated sodium bicarbonate. The resulting mixture is transferred to a separatory funnel containing 200 ml of water and in the separatory funnel the oil phase is separated from the aqueous phase. The aqueous phase is extracted with one portion (30 ml) of methylene dichloride and the extract is combined with the oil layer. The resulting material is dried over anhydrous sodium sulphate, filtered and then stripped at atmospheric pressure and 80° C. The resulting product is then distilled through a micro Vigreaux column yielding the following fractions:

| Fraction | Vapor Temp. | Liquid Temp. | Vacuum mm |
|---|---|---|---|
| 3 | 131 | 160 | 2.0 |
| 4 | 147 | 170 | 2.0 |
| 5 | 150 | 175 | 1.9 |
| 6 | 154 | 205 | 1.9 |

This material is then redistilled through a micro Vigreaux column yielding the following fractions:

| Fraction | Vapor Temp. | Liquid Temp. | Vacuum Temp. | Weight (g) |
|---|---|---|---|---|
| 1 | 132/147 | 145/149 | 1.6/1.6 | 2.4 |
| 2 | 148 | 150 | 1.6 | 7.0 |
| 3 | 148 | 151 | 1.6 | 12.3 |
| 4 | 147 | 190 | 1.6 | 2.2 |

Fractions 1–4, inclusive are then bulked for use in Examples 3 and 4.

FIG. 8 represents the GC profile for the reaction mass one hour and 52 minutes after the addition of diacetyl dimer for Batch #1 (conditions: 25% SE-30 column programmed at 150—220° C. at 8° C. per minute).

FIG. 9 represents the GC profile for Batch #1 where the reaction mass was heated for 6 hours and 20 minutes at 50° C. after which time it was allowed to remain at 25° C. for a period of 16 hours after addition of the diacetyl dimer (Conditions: 25% SE-30 column operated at 150—220° C. at 8° C. per minute).

EXAMPLE III

Use In Coffee Flavors of 5-Acetyl-2-(Furfurylthio)Dihydro-2,5-Dimethyl-3-[2H]Furanone "Cafeol" a natural concentrated coffee extract produced by Mero Aromatics, of New York, N.Y., it is made up into a 0.1% solution. This solution is divided into 2 portions. To a first portion at the rate of 0.02 ppm is added 5-acetyl-2-(furfurylthio) dihydro-2,5-dimethyl-3-[2H]furanone. To the second portion nothing is added. Both the portion with and the portion without the 5-acetyl-2-(furfurylthio) dihydro-2,5-dimethyl-3-[2H]furanone are compared by a bench panel of 5 individual expert tasters. The coffee extract solution with the addition of the 5-acetyl-2-(furfurylthio)dihydro-2,5-dimethyl-3-[2H] furanone is indicated by the bench panel to have a substantially stronger coffee aroma and taste and is therefor unanimously preferred by all the tasters of the bench panel.

EXAMPLE IV

Use In Coffee Flavors Of
5-Acetyl-2-(Furfurylthio)dihydro-2,5-Dimethyl-3-[2H]Furanone The following basic coffee flavor formulation is prepared:

| Ingredients | Parts by Weight |
|---|---|
| Diacetyl (10% in 95% food grade aqueous ethanol) | 1 |
| Benzaldehyde | 1 |
| Furfural | 0.5 |
| Furfural Propionate | 10 |
| Trimethyl Pyrazine (10% in 95% aqueous food grade ethanol) | 1 |
| 2,6-Dimethoxy phenol | 2 |
| Pyruvic acid | 15 |
| Furfural Mercaptan (1% soluton in 95% food grade ethanol) | 1.0 |
| Furfural acetate | 0.5 |
| Propylene glycol | 68 |

The foregoing formulation is divided into 2 parts. The first part 0.2% by weight of 5-acetyl-2-(furfurylthio)dihydro-2,5-dimethyl-3-[2H]furanone prepared according to Example II is added. To the other portion nothing is added. Both formulations are compared in water at the rate of 20 ppm. The coffee flavor with the 5-acetyl-2-(furfurylthio)dihydro-2,5-dimethyl-3-[2H]furanone has a fresh roasted aroma and better coffee taste. Therefor a panel of expect tasters prefers the flavor with the 5-acetyl-2-(furfurylthio)dihydro-2,5-dimethyl-3-[2H]furanone as more characteristic and more natural coffee-like.

EXAMPLE V

A. Powder Flavor Composition

20 Grams of the flavor composition of Example IV is emulsified in a solution containing 300 grams gum acacia and 700 grams water. The emulsion is spraydried with a Bowen Lab Model Drier utilizing 260 c.f.m. of air with an inlet temperature of 500° F., an outlet temperature of 200° F., and a wheel speed of 50,000 r.p.m.

B. Sustained Release Flavor

The following mixture is prepared:

| Ingredient | Parts by Weight |
|---|---|
| Liquid Coffee Flavor Composition of Example IV | 20 |
| Propylene glycol | 9 |
| Cab-O-Sil® M-5 (Brand of Silica produced by the Cabot Corporation of 125 High Street, Boston, Mass. 02110; Physical Properties: Surface Area: 200 m²/gm Nominal particle size: 0.012 microns Density: 2.3 lbs/cu.ft.) | 5.00 |

The Cab-O-Sil is dispersed in the liquid coffee flavor composition of Example IV with vigorous stirring, thereby resulting in a viscous liquid. 71 Parts by weight of the powder flavor composition of Part A, supra, is then blended into the said viscous liquid, with stirring at 25°C. for a period of 30 minutes resulting in a dry, free flowing sustained release flavor powder.

EXAMPLE VI

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid coffee flavor composition of Example IV is added to the solution which is then homogenized to form an emulsion having a particle size typically in the range of 5–40 microns. This material is kept at 120° F. under which conditions the gelatin will not jell.

Coascervation is induced by adding, slowly and uniformly, 40 parts by weight of a 20% aqueous solution of sodium sulphate. During coascervation, the gelatin molecules are deposited uniformly about each oil droplet as a nucleus.

Gelation is effected by pouring the heated coascervate mixture into 1,000 parts by weight of 7% aqueous solution of sodium sulphate at 65° F. The resulting jelled coascervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE VII

Chewing Gum 100 parts by weight of chicle are mixed with 4 parts by weight of the flavor prepared in accordance with Example V. 300 Parts of sucrose and 100 parts of corn syrup are added. Mixing is effected in a ribbon blender with jacketed side walls of the type manufactured by the Baker Perkins Co.

The resulting chewing gum blend is then manufactued into strips 1 inch in width and 0.1 inches in thickness. The strips are cut into lengths of 3 inches each. On chewing, the chewing gum has a pleasant long lasting coffee flavor.

EXAMPLE VIII

Chewing Gum

100 Parts by weight of chicle are mixed with 18 parts by weight of the flavor prepared in accordance with Example VI. 300 Parts of sucrose and 100 parts of corn syrup are then added. Mixing is effected in a ribbon blender with jacketed side walls of the type manufactured by the Baker Perkins Co.

The resulting chewing gum blend is then manufactured into strips 1 inch in width and 0.1 inches in thickness. The strips are cut into lengths of 3 inches each. On chewing, the chewing gum has a pleasant long lasting coffee flavor.

EXAMPLE IX

Toothpaste Formulation

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |

-continued

| Parts by Weight | Ingredient |
|---|---|
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example VI |
| 100.00 (Total) | |

Procedure:
1. The ingredients in Group "A" are stirred and heated in a steam jacketed kettle to 160° F.
2. Stirring is continued for an additional three to five minutes to form a homogenous gel.
3. The powders of Group "B" are added to the gel, while mixing until a homogenous paste is formed.
4. With stirring, the flavor of "D" is added and lastly the sodium n-lauroyl sarcosinate.
5. The resultant slurry is then blended for one hour. The completed paste is then transferred to a three roller sill and then homogenized, and finally tubed.

The resulting toothpaste when used in a normal toothbrushing procedure yields a pleasant coffee flavor of constant strong intensity throughout said procedure (1-1.5 minutes).

EXAMPLE X

Chewable Vitamin Tablets

The flavor material produced according to the process of Example V is added to a Chewable Vitamin Tablet Formulation at a rate of 10 mg/gm which Chewable Vitamin Tablet Formulation is prepared as follows:

In a Hobart Mixer, the following materials are blended to homogeneity:

| | Gms/1000 Tablets |
|---|---|
| Vitamin C (ascorbic acid) as ascorbic acid-sodium ascorbate mixture 1:1 | 70.0 |
| Vitamin B$_1$ (thiamine mononitrate) as Rocoat$^R$ thiamine mononitrate 33 1/3% | 4.0 |
| Vitamin B$_2$ (roboflavin) as Rocoat$^R$ riboflavin 33 1/3% | 5.0 |
| Vitamin B$_6$ (pyridoxine hydrochloride) as Rocoat$^R$ pyridoxine hydrochloride 33 1/3% | 4.0 |
| Niacinamide as Rocoat$^R$ niacinamide 33 1/3% | 33.0 |
| Calcium pantothenate | 11.5 |
| Vitamin B$_{12}$ (cyanocobalamin) as Merck 0.1% in gelatin | 3.5 |
| d-Biotin | 0.044 |
| Certified lake color | 5.0 |
| Flavor of Example V | 10.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, long-lasting, consistently strong coffee flavor for a period of 12 minutes.

EXAMPLE XI

Chewing Tobacco

Onto 100 pounds of tobacco for chewing (85% Wisconsin leaf and 15% Pennsylvania leaf) the following casing is sprayed at a rate of 30%:

| Ingredients | Parts by Weight |
|---|---|
| Corn Syrup | 60 |
| Licorice | 10 |
| Glycerine | 20 |
| Fig Juice | 4.6 |
| Prune Juice | 5 |
| Flavor Material of Example VI | 0.4 |

The resultant product is redried to a moisture content of 20%. On chewing, this tobacco has an excellent substantially consistent, long-lasting caramel/tobacco/nutty (20 minutes) nuance in conjunction with the main natural tobacco note.

EXAMPLE XII

Tobacco Containing 5-Acetyl-2-(Furfurylthio)dihydro-2,5-Dimethyl-3-[2H]Furanone

The following tobacco flavor formulation (A) is prepared:

| Ingredients | Parts by Weight |
|---|---|
| Ethyl Butyrate | 0.05 |
| Ethyl Valerate | 0.05 |
| Maltol | 2.00 |
| Cocoa Extract | 26.00 |
| Coffee Extract | 10.00 |
| Ethanol (95% aqueous, food grade) | 20.00 |
| Water | 41.90 |

The following tobacco formulation (B) is prepared:

| Ingredients | Parts by Weight |
|---|---|
| Bright Tobacco | 40.1 |
| Burley Tobacco | 24.0 |
| Maryland Tobacco | 1.1 |
| Turkish Tobacco | 11.6 |
| Stem (Flue-cured) Tobacco | 14.2 |
| Glycerin | 2.8 |
| Water | 5.3 |

The flavor formulation (A) is added to a portion of the smoking tobacco formulation (B) at the rate of 0.1% by weight of the tobacco. The flavored and non-flavored tobacco formulations are then formulated into cigarettes by the usual manufacturing procedures.

At the rate of 20 ppm to half of the cigarettes in each group is added 5-acetyl-2-(furfurylthio)dihydro-2,5-dimethyl-3-[2H]furanone produced according to the process of Example II. The use of the 5-acetyl-2-(furfurylthio)dihydro-2,5-dimethyl-3-[2H]furanone in the cigarettes causes the cigarettes prior to smoking to have a "cigarette pack" aroma and a coffee like aroma and taste prior to smoking. In smoke flavor the cigarettes containing the 5-acetyl-2-(furfurylthio)dihydro-2,5-dimethyl-3-[2H]furanone have sweet, caramel/coffee-like tastes with nutty/pyrazine nuances and roasted nut-like nuances. Each of the tobacco articles containing the 5-acetyl-2-(furfurylthio)dihydro-2,5-dimethyl-3-[2H]furanone whether or not containing other flavor ingredients of Formulation "A" have enhanced tobacco aroma and taste.

Similar experiment is carried out as above except that instead of a mixture of isomers of 5-acetyl-2-(furfurylthio)dihydro-2,5-dimethyl-3-[2H]furanone of Example II being used, the mixture of isomers of 5-acetyl-2-(furfurylthio)dihydro-2,5-dimethyl-3-[2H]furanone of Example I is used in this latter case at 100 ppm the 5-acetyl-2-(furfurylthio)dihydro-2,5-dimethyl-3-[2H]furanone imparts body to its Burley and black tobacco notes rather than Virginia tobacco notes. In addition, coffee, cocoa and licorice nuances are present in the cigarettes to which the 5-acetyl-2-(furfurylthio)dihydro-2,5-dimethyl-3-[2H]furanone is added.

EXAMPLE XIII

Tobacco Flavor Formulation

A tobacco flavor formulation is prepared by admixing the following ingredients:

| Ingredients | Parts by Weight |
| --- | --- |
| 5-acetyl-2-(furfurylthio) dihydro-2,5-dimethyl-3-[2H]furanone mixture of isomers produced according Example II | 0.14 |
| Bergamot Oil Italy | 5.00 |
| Ylang Ylang Oil | 1.20 |
| 2-(2'-methyl-n-propyl)-4,5-dimethyl-Δ³-thiazoline | 1.40 |
| Acetophenone | 1.20 |
| Phenylacetaldehyde | 0.50 |
| Phenylethylisovalerate | 1.00 |
| Methylheptylcarbonate | 0.50 |
| 3-Phenyl-4-pentenaldiethyl acetal | 20.00 |
| Aqueous food grade ethanol 95% | 69.40 |

The foregoing flavor is added to smoking tobacco at the rates of 0.10%, 0.20% and 0.30% based on the weight of dried tobacco. The tobacco is then manufactured into cigarettes according to standard manufacturing practice. The purpose of the 3-phenyl-4-pentenaldiethylacetal is to cause the tobacco on smoking to have a hay, clover-like flavor with fruity notes. The purpose of the 2-(2'-methyl-n-propyl)-4,5-dimethyl-Δ³-thiazoline (at concentrations based on the dry weight of tobacco of 200 ppm) is to act to supply strong, intense long-lasting "Bright" notes to the previously blended tobacco flavor formulation. The purpose of the use of the 5-acetyl-2-(furfurylthio)dihydro-2,5-dimethyl-3-[2H]furanone isomer mixture is to add more body and more aroma to the tobacco adding burley and black tobacco notes rather than Virginia notes. In addition, coffee/caramel, cocoa and licorice nuances are added to the taste of the tobacco as well as its aroma on smoking. The level of the 5-acetyl-2-(furfurylthio)dihydro-2,5-dimethyl-3-[2H]furanone in the cigarettes is, respectively, 10 ppm, 20 ppm and 30 ppm.

EXAMPLE XIV

Preparation of
2,5-Diethyl-4-Methyl-5-Propionyl-2-(Furfurylthio)-dihydro-3-[2H]Furanone Reaction:

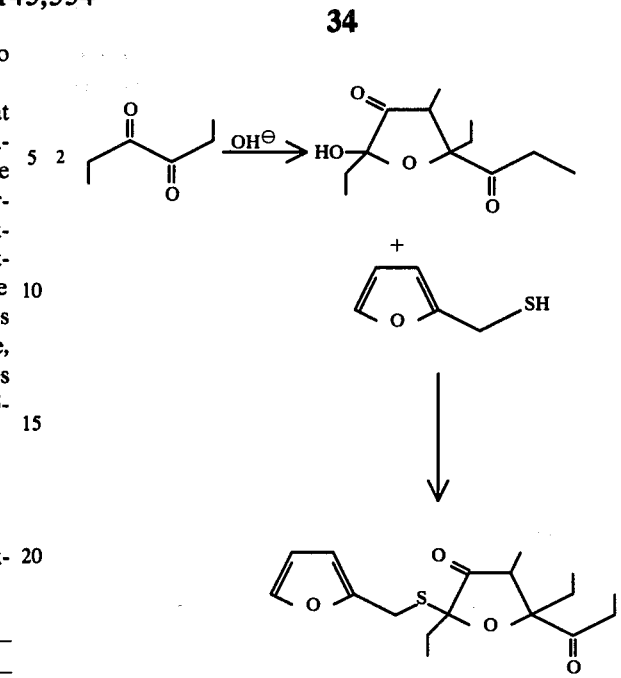

Into a 5 liter reactor equipped with a stirrer, therometer, reflux condenser and cooling coils are placed the following ingredients:

3,4-hexanedione: 320 grams
water: 3200 ml

The resulting mixture is cooled to 3° C. and over a period of 20 minutes is added a mixture of 54.4 grams of KOH dissolved in 1600 ml water. Subsequent to the addition of the KOH solution, 85 grams of 50% sulfuric acid is added to the mixture to bring the pH to 5. 1600 grams of sodium chloride is added thereby rendering the resulting mixture saturated with sodium chloride. The mixture is then extracted with four 200 ml portions of methylenedichloride and then the extracts are dried over anhydrous sodium sulfate. The methylenedichloride is stripped at atmospheric pressure and 80° C. and the resulting oil is distilled through a 6 inch Vigreux column followed by redistillation through the same column to yield the dimer of 3,4-hexanedione.

Into a 250 ml reactor equipped with stirrer, thermometer, heating mantle and reflux condenser is placed 20 grams (17.7 ml) furfuryl mercaptan, 10 ml tetrahydrofuran and 0.5 ml concentrated hydrochloric acid. The resulting mixture is heated to 50° C. and, over a 10 minute period is added 35 grams of the dimer of 3,4-hexanedione dissolved in 20 grams tetrahydrofuran. The separatory funnel from which this material is added is then rinsed out with an additional 20 ml tetrahydrofuran which is then added to the reaction mass. The reaction mass is then stirred for a period of 5 hours at 50° C. with GC samples taken each hour. 20 ml Saturated sodium bicarbonate solution is then added and the reaction mass is transferred to a separatory funnel containing 100 ml water. The oil phase is separated from the aqueous phase. The aqueous phase is then extracted with one 30 ml portion of methylenedichloride and combined with the oil phase. The combined oil phase is then dried over anhydrous sodium sulphate and filtered. The methylenedichloride is stripped at atmospheric pressure to 80° C. and the resulting product is distilled through a micro Vigreux column. NMR. IR and mass spectral analyses confirm that the resulting product has the structure:

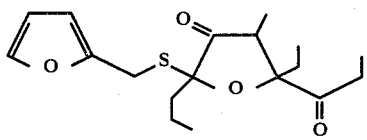

What is claimed is:

1. A process for preparing at least one 5-acyl-2-(furfurylthio)dihydro-2,5-dialkyl-3-[2H]furanone having the structure:

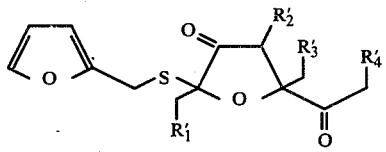

wherein $R_1'$, $R_2'$, $R_3'$ and $R_4'$ are the same or different and each represents hydrogen or methyl comprising the steps of (i) First reacting an alpha, beta diketone having the structure:

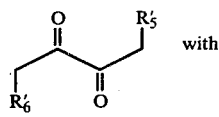
with furfuryl mercaptan having the structure:

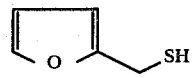

thus forming an addition product having the structure:

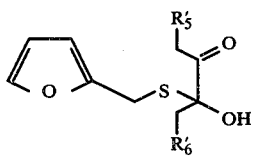

(ii) and then reacting the said addition product with an alpha, beta diketone having the structure:

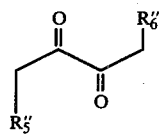

thereby forming said 5-acyl-(furfurylthio) dihydro-2,5-dialkyl-3-[2H]furanone wherein $R_5'$ and $R_6'$ are the same or different and each represents methyl or hydrogen; and wherein $R_5''$ and $R_6''$ are the same or different and each represents hydrogen or methyl; and wherein the number of methyl groups constituting $R_1'$, $R_2'$, $R_3'$ and $R_4'$ is the same as the number of methyl groups constituting $R_5'$, $R_6'$, $R_5''$ and $R_6''$.

* * * * *